(12) United States Patent
Mazanec et al.

(10) Patent No.: US 9,249,080 B2
(45) Date of Patent: Feb. 2, 2016

(54) CHEMICAL INTERMEDIATES BY CATALYTIC FAST PYROLYSIS PROCESS

(71) Applicant: Anellotech, Inc., Pearl River, NY (US)

(72) Inventors: Terry Mazanec, Solon, OH (US); Eugene Schmelzer, Baltimore, MD (US); Fred Pesa, Auroroa, OH (US); Dennis McCullough, Houston, TX (US); Ruozhi Song, Wilmington, DE (US); Yu-Ting Cheng, Amherst, MA (US)

(73) Assignee: Anellotech, Inc., Pearl River, NY (US)

( * ) Notice: Subject to any disclaimer, the term of this patent is extended or adjusted under 35 U.S.C. 154(b) by 0 days.

(21) Appl. No.: 14/056,723

(22) Filed: Oct. 17, 2013

(65) Prior Publication Data

US 2014/0107306 A1    Apr. 17, 2014

Related U.S. Application Data

(60) Provisional application No. 61/715,248, filed on Oct. 17, 2012.

(51) Int. Cl.
*C08G 63/183* (2006.01)
*C10G 1/00* (2006.01)
(Continued)

(52) U.S. Cl.
CPC .............. *C07C 51/31* (2013.01); *B29C 43/003* (2013.01); *B29C 49/0005* (2013.01); *C07C 1/22* (2013.01); *C07C 2/66* (2013.01); *C07C 2/864* (2013.01); *C07C 5/10* (2013.01); *C07C 5/333* (2013.01); *C07C 7/00* (2013.01); *C07C 29/15* (2013.01); *C07C 29/20* (2013.01); *C07C 37/50* (2013.01); *C07C 37/58* (2013.01); *C07C 37/68* (2013.01); *C07C 45/006* (2013.01); *C07C 45/28* (2013.01); *C07C 45/78* (2013.01); *C07C 51/42* (2013.01); *C08F 12/08* (2013.01); *C08F 212/08* (2013.01); *C08F 212/10* (2013.01); *C08G 63/183* (2013.01); *C08G 63/80* (2013.01); *C10G 1/002* (2013.01); *C10G 1/02* (2013.01); *C10G 3/40* (2013.01); *C10G 3/42* (2013.01);
(Continued)

(58) Field of Classification Search
CPC ...... C08G 63/183; C10G 1/002; C07C 35/58; C07C 51/54
USPC ............... 526/75; 528/308.3, 308.8; 549/248; 568/806; 585/240, 440
See application file for complete search history.

(56) References Cited

U.S. PATENT DOCUMENTS 5,504,259 A * 4/1996 Diebold et al. ............... 568/697
8,735,515 B2    5/2014 Cooper et al.
(Continued)

FOREIGN PATENT DOCUMENTS

WO    WO 2008/109877    9/2008
WO    WO 2011/031320    3/2011

OTHER PUBLICATIONS

Huber, G.W., et al., "Synthesis of Transportation Fuels from Biomass: Chemistry, Catalysts, and Engineering," Chem. Rev. 106 (2006), pp. 4044-4098.
(Continued)

*Primary Examiner* — Fred M Teskin
(74) *Attorney, Agent, or Firm* — Frank Rosenberg

(57) ABSTRACT

In this invention, a portion of the products from a pyrolysis reactor are reacted in a process to form one or more chemical intermediates.

18 Claims, 2 Drawing Sheets

(51) Int. Cl.

| | | |
|---|---|---|
| *C08F 12/08* | (2006.01) | |
| *C07C 37/58* | (2006.01) | |
| *C07C 51/42* | (2006.01) | |
| *C07C 51/31* | (2006.01) | |
| *C10G 29/20* | (2006.01) | |
| *C10G 57/00* | (2006.01) | |
| *C10G 1/02* | (2006.01) | |
| *C10G 3/00* | (2006.01) | |
| *C10G 45/44* | (2006.01) | |
| *C10G 50/00* | (2006.01) | |
| *C10G 9/00* | (2006.01) | |
| *B29C 43/00* | (2006.01) | |
| *B29C 49/00* | (2006.01) | |
| *C07C 1/22* | (2006.01) | |
| *C07C 2/66* | (2006.01) | |
| *C07C 2/86* | (2006.01) | |
| *C07C 5/10* | (2006.01) | |
| *C07C 5/333* | (2006.01) | |
| *C07C 7/00* | (2006.01) | |
| *C07C 29/15* | (2006.01) | |
| *C07C 29/20* | (2006.01) | |
| *C07C 37/50* | (2006.01) | |
| *C07C 37/68* | (2006.01) | |
| *C07C 45/00* | (2006.01) | |
| *C07C 45/28* | (2006.01) | |
| *C07C 45/78* | (2006.01) | |
| *C08F 212/08* | (2006.01) | |
| *C08F 212/10* | (2006.01) | |
| *C08G 63/80* | (2006.01) | |
| *B29K 67/00* | (2006.01) | |

(52) U.S. Cl.
CPC ............... *C10G 9/00* (2013.01); *C10G 29/205* (2013.01); *C10G 45/44* (2013.01); *C10G 50/00* (2013.01); *C10G 57/005* (2013.01); *B29K 2067/003* (2013.01); *C10G 2400/20* (2013.01); *C10G 2400/22* (2013.01); *C10G 2400/30* (2013.01)

(56) References Cited

U.S. PATENT DOCUMENTS

| | | | |
|---|---|---|---|
| 2009/0227823 A1* | 9/2009 | Huber et al. | 585/324 |
| 2009/0246430 A1 | 10/2009 | Kriegel et al. | |
| 2010/0028512 A1 | 2/2010 | Kriegel et al. | |
| 2011/0262669 A1 | 10/2011 | Kriegel et al. | |
| 2013/0131409 A1* | 5/2013 | Keusenkothen et al. | 585/251 |

OTHER PUBLICATIONS

Bain, Richard L., "An Introduction to Biomass Thermochemical Conversion", presented at the DOE/NASLUGC Biomass and Solar Energy Workshops, National Renewable Energy Laboratory, Aug. 3-4, 2004.

Tushar P. Vispute, et al. "Renewable Chemical Commodity Feedstocks from Integrated Catalytic Processing of Pyrolysis Oils", Science 330, 1222 (2010); DOI: 10.1126/Science. 1194218.

Dickerson, Theodore, et al. "Catalytic Fast Pyrolysis: A Review", Energies 2013, 6, 514-538; doi: 10.3390/en6010514.

Lappas, A.A., "Biomass pyrolysis in a circulating fluid bed reactor for the production of fuels and chemicals", Fuel 81 (2002) 2087-2095.

\* cited by examiner

CHEMICAL INTERMEDIATES BY CATALYTIC FAST PYROLYSIS PROCESS

RELATED APPLICATION

This application claims the benefit of priority to U.S. Provisional Patent Application Ser. No. 61/715,248, filed Oct. 17, 2012.

INTRODUCTION

Chemical intermediates are normally derived from fossil resources such as oil, natural gas, or coal in multi-step processes. In order to replace or supplement the production of chemical intermediates from fossil resources, it will be necessary to develop processes that originate from fresh (non-fossil) biological resources, i.e., biomass. The present invention provides methods and systems for making chemical intermediates from biomass.

Several workers have proposed using biomass-derived products as intermediates for making certain polymers. For example, Kriegel et al. in US 2010/0028512 suggest using biomass-derived ethylene to form polyethylene. Kriegel et al. in US 2009/0246430 and US 2011/0262669 describe using biomass-derived ethylene glycol to form PET (polyethylene terephthlate polymer). Kriegel et al. also suggest using biomass-derived terephthalic acid, isophthalic acid, or dimethyl terephthlate. Likewise, Cooper et al. in US 2012/0046427 discuss routes for making polystyrene or PET from biomass-derived intermediates such as ethylene, benzene, and p-xylene.

Cortright et al. in WO 2008/109877 discuss the use of oxygenated hydrocarbons to form a variety of chemical compounds. In some cases, the oxygenates could be derived from pyrolysis. Cortright et al. propose the formation of a myriad of compounds including cyclohexane among thousands of other compounds.

It is well known that a variety of biomass-derived polymeric materials such as lignin, cellulose, and hemi-cellulose, can be pyrolyzed to produce mixtures of aromatics, olefins, CO, CO2, water, and other products. A particularly desirable form of pyrolysis is known as catalytic fast pyrolysis (CFP), developed by Professor George Huber, and involves the conversion of biomass in a catalytic fluid bed reactor to a mixture of aromatics, olefins, CO, CO2, char, ash, and a variety of other organics. The aromatics include benzene, toluene, xylenes, and naphthalene (BTXN), among other aromatics. The olefins include ethylene (30-60% of olefins), propylene (30-50%), and lesser amounts of higher olefins. BTXN have high value and are easily transported.

It is an object of this invention to provide methods for the production of chemical intermediates from the primary products of CFP (i.e., aromatics, olefins, CO) that can be integrated with CFP in advantageous ways that improve the overall yield of intermediates, improve the thermal balance, generate useful and different by-products, and/or generate integrated processes for the production of chemicals from renewable resources. For example, it is an object of this invention to provide integrated processes for the production of ethylene oxide, ethanol, acetic acid, acetaldehyde, styrene, cumene, terephthalic acid, phthalic anhydride, phenol. ethylbenzene, cyclohexane, adipic acid, benzaldehyde, toluene diisocyanate, toluene diamine, methylene diphenyl diisocyanate, polyurethanes, polycarbonates, and other chemical intermediates by the conversion of benzene, toluene, xylenes, naphthalene, ethylene, propylene and butylenes prepared by catalytic fast pyrolysis.

SUMMARY OF THE INVENTION

Generally, the invention includes and of the methods, apparatus and systems that are described herein; particularly involving pyrolysis of biomass and conversion of at least one pyrolysis product to another chemical compound.

In one aspect, the invention provides a method for producing one or more fluid hydrocarbon products from a hydrocarbonaceous material comprising feeding a hydrocarbonaceous material to a reactor, and pyrolyzing within the reactor at least a portion of the hydrocarbonaceous material under reaction conditions sufficient to produce one or more pyrolysis products, catalytically reacting at least a portion of the pyrolysis products, separating at least a portion of the hydrocarbon products, and reacting a portion of said hydrocarbon products to produce a chemical intermediate. Preferably, all of these steps are conducted within an integrated reactor system. An integrated reactor system is defined as comprising both apparatus and chemical composition(s) within the apparatus.

In the present invention, a preferred apparatus comprises a biomass conveyor, a catalyst-containing pyrolysis reactor, a primary product separator, a primary product upgrader, and a secondary product separator. At least a portion of the primary products comprise aromatics and/or olefins. The secondary products, also called chemical intermediates, comprise ethylene oxide, ethanol, acetic acid, acetaldehyde, acrylonitrile, acrylic acid, styrene, cumene, ethyl benzene, terephthalic acid, dimethyl terephthalate, polyethyleneterephthalate (PET), polybutylene terephthalate, phthalic anhydride, phenol, ethylbenzene, cyclohexane, adipic acid, benzaldehyde, benzoic acid, hexanes, ethylene glycol, polyethylene, hexamethylenediamine, adiponitrile, Nylon 6, Nylon 6,6, toluene diisocyanate, toluene diamine, methylene diphenyl diisocyanate, polyurethanes, polycarbonates, alkylphenols, polymethylphenols, ethylphenols, isopropylphenols, sec-butylphenols, tert-butylphenols, tert-pentylphenols, cycloalkylphenols, aralkylphenols, alkenylphenols, indanols, catechol, trihydroxybenzenes, pyrogallol, hydroxyhydroquinone, phloroglucinol, bisphenols (bishydroxyarylalkanes), hydroxybiphenyls, phenol ethers and mixtures thereof. In some embodiments, at least a portion of: the primary products, and/or partially deactivated catalyst from a catalytic fast pyrolysis reactor, and/or secondary products, or some combination of these, are oxidized to provide heat for the biomass upgrading process. In some embodiments the chemical intermediate products are processed by processes such as blow-molding, extrusion, stamping, pressing or otherwise to form bottles, sheets, fibers, plates, or other useful shapes.

The invention can be further characterized by one or more (that is, any combination) of the following features: at least a portion of the byproducts of the chemical intermediate production are returned to the pyrolysis reactor; at least a portion of one benzene-rich fraction separated from the hydrocarbon products is alkylated with an olefin to produce a chemical intermediate (in some preferred embodiments, an olefin produced from the catalytic fast pyrolysis process is used at least in part for the alkylation; in some preferred embodiments the olefin comprises ethylene and/or propylene); at least a portion of one benzene-rich fraction separated from the hydrocarbon products is oxidized to produce phenol; at least a portion of one benzene-rich fraction separated from the hydrocarbon products is hydrogenated to produce cyclohexane, and in some embodiments at least a portion of the cyclohexane is oxidized to adipic acid (in some embodiments, the adipic acid is polymerized in the same integrated system); at least a portion of one toluene-rich fraction separated from the hydrocarbon products is subjected to a disproportionation reaction to produce a xylenes-enriched product stream; at least a portion of one toluene-rich fraction separated from the hydrocarbon products is subjected to a methylation reaction to produce a xylenes-enriched product stream; at least a portion of one para-xylene-rich fraction separated from, or otherwise derived from the hydrocarbon products is oxidized to produce terephthalic acid that, optionally is polymerized to poly(ethylene terephthalate) (PET), poly(butylene terephthalate) (PBT), or poly(trimethylene terephthalate) (PTT); at least a portion of one ortho-xylene rich fraction separated from the hydrocarbon products is oxidized to produce phthalic anhydride (in some embodiments, at least a portion of the phthalic anhydride is esterified to produce a phthalate diester; at least a portion of one ethylbenzene-rich fraction separated from, or otherwise derived from the hydrocarbon products is dehydrogenated to produce styrene that, optionally, is polymerized to polystyrene; the fluid hydrocarbon products comprise olefins (preferably combined with a step of polymerizing the olefins or reacting the olefins with aromatics); the fluid hydrocarbon products comprise aromatics (which may be alkylated) and the aromatics are subjected to one or more of the following: dehydrogenation (optionally followed by polymerization), hydrogenated to paraffins, or oxidized to acids, anhydrides, aldehydes, alcohols or epoxides (the epoxides may be subsequently polymerized).

The invention also provides a method for producing one or more fluid hydrocarbon products from a hydrocarbonaceous material comprising: feeding a hydrocarbonaceous material to a reactor; pyrolyzing within the reactor at least a portion of the hydrocarbonaceous material under reaction conditions sufficient to produce one or more pyrolysis products; catalytically reacting within the reactor at least a portion of the one or more pyrolysis products under reaction conditions sufficient to produce one or more fluid hydrocarbon products comprising olefins and aromatics; reacting at least a portion of said fluid hydrocarbon products to produce at least one chemical intermediate; and feeding at least a portion of the byproducts of the chemical intermediate production back to the pyrolysis reactor.

In some embodiments, the methods use a recycle step in which the recycled compounds do not consist primarily of olefins, nor of compounds produced during catalyst regeneration.

The invention also provides for a method of oxidizing p-xylene using pyrolysis products other than acetic acid.

Another concept is for a method of sequestering carbon comprising converting biomass to polystyrene, forming cups from the polystyrene, and burying or recycling the cups. In some preferred embodiments, the polystyrene is formed in the same facility in which biomass is pyrolyzed. In this fashion, consumers can use disposable polystyrene cups while being assured that the cups do not contribute to increased carbon in the atmosphere. As in any of the inventive methods, the presence of biomass-derived materials can be confirmed by measuring the presence of $^{14}C$ in the material.

The invention includes methods, apparatus, and systems (which comprise apparatus plus process streams (that is, fluid compositions) and may further be characterized by conditions such as temperature or pressure). Thus, any of the descriptions herein apply to the inventive methods, apparatus and systems.

The hydrocarbonaceous material that is fed to the reactor typically comprises a solid hydrocarbonaceous material, often in the presence of a gas phase. In some preferred embodiments, the hydrocarbonaceous material is at least 90 mass % solids. In some lesser preferred embodiments the hydrocarbonaceous material could be only in the gas and/or a liquid or slurry phase. In some embodiments, a recycle stream, preferably an aqueous recycle stream, can be contacted with the hydrocarbonaceous material before the hydrocarbonaceous material is fed to the reactor.

In preferred embodiments of the inventive method, apparatus, and/or system, the pyrolysis reactor contains a solid catalyst. The solid catalyst preferably comprises a zeolite, more preferably a zeolite and a metal and/or a metal oxide. The solid catalyst in the CFP reactor may comprise elements such as, for example, silicon, aluminum, titanium, vanadium, chromium, manganese, iron, cobalt, nickel, copper, zinc, gallium, platinum, palladium, silver, tin, phosphorus, sodium, potassium, magnesium, calcium, tungsten, zirconium, cerium, lanthanum, and combinations thereof. Additional catalyst materials or inert solids may also be present. In some preferred embodiments, the CFP reaction is catalyzed by a zeolite. In some embodiments, the zeolite comprises pore sizes in the range of 5.0 to 6.5 angstroms. In some preferred embodiments, the catalyst comprises ZSM5. In some preferred embodiments, the mass ratio of catalyst fed to the reactor to hydrocarbonaceous material fed to the reactor is between 0.1 and 20.

In some embodiments, an aqueous phase is recovered from the CFP reactor and carbonaceous material is removed from the aqueous phase and at least a portion of the separated carbonaceous materials is recycled to the CFP reactor. Preferably, the separated carbonaceous phase comprises olefins, aromatics, or oxygenates, or a mixture of these, and at least a portion of these are fed to the CFP reactor. This can be done, for example, by a stripping process in which a liquid phase is contacted with a gas (such as by bubbling a gas through the liquid) and the resulting gas phase, which is enriched with at least one component from the liquid phase, is passed into the reactor. Alternatively, the liquid phase can be stripped and then the liquid phase, now at least partly depleted of at least one component, is recycled to the reactor. As with any of the recycle steps, the return flow may be directly into the reactor or at any stage in a flow path prior to the reactor stage.

In preferred embodiments, the CFP reactor is a fluidized bed, circulating bed, or riser reactor. In some preferred embodiments, the temperature within the reactor is between 300 and 1000° C.

The hydrocarbonaceous material fed to the reactor may comprise a biomass material; or plastic waste, recycled plastics, agricultural and municipal solid waste, food waste, animal waste, carbohydrates, or lignocellulosic materials; or the hydrocarbonaceous material can comprise xylitol, glucose, cellobiose, cellulose, hemi-cellulose, or lignin; or the hydrocarbonaceous material may comprise sugar cane bagasse, glucose, wood, or corn stover, or any of these materials in any combination.

In any of the inventive aspects, the pyrolysis step(s), (and/or any selected process step) may preferably be conducted at a pressure (absolute) of 30 atm or less, more preferably of less than 10 atm, in some embodiments less than 1 atm; and in some embodiments in the range of 0.1 to 10 atm.

DETAILED DESCRIPTION OF THE INVENTION

Glossary

Aromatics

Figure 1:
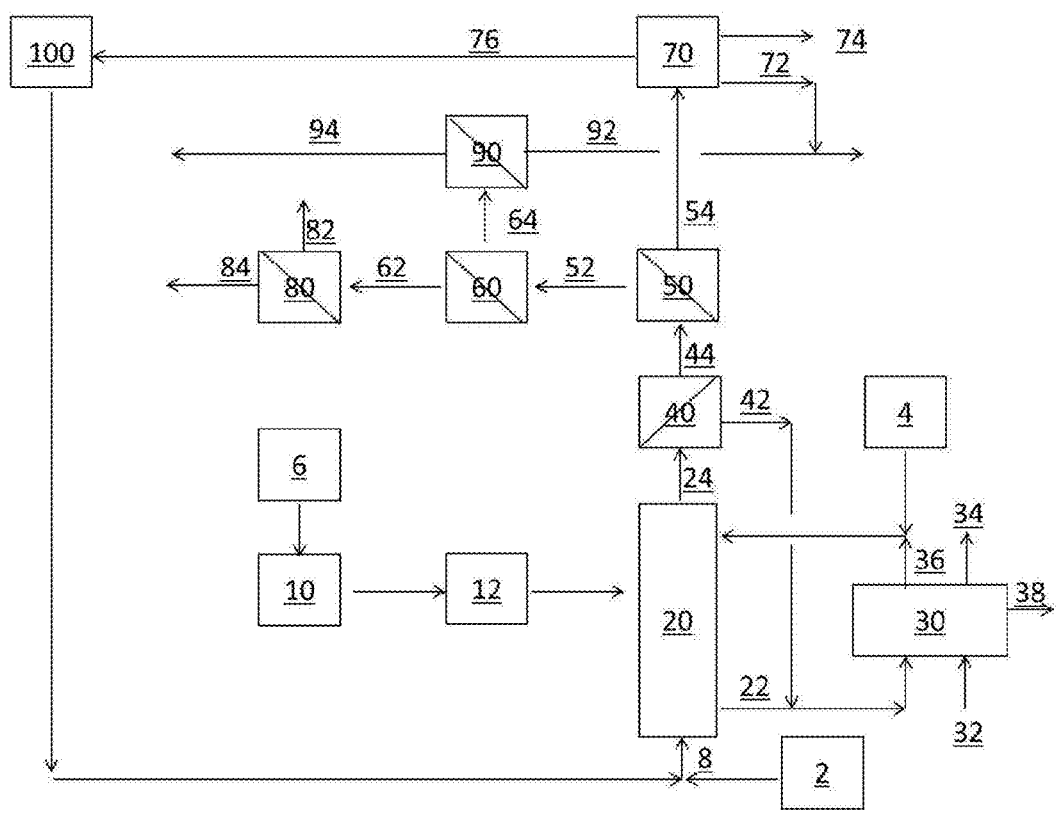
FIG. 1 illustrates the catalytic fast pyrolysis process.

As used herein, the terms "aromatics" or "aromatic compound" are used to refer to a hydrocarbon compound or compounds comprising one or more aromatic groups such as, for example, single aromatic ring systems (e.g., benzyl, phenyl, etc.) and fused polycyclic aromatic ring systems (e.g. naphthyl, 1,2,3,4-tetrahydronaphthyl, etc.). Examples of aromatic compounds include, but are not limited to, benzene, toluene, indane, indene, 2-ethyl toluene, 3-ethyl toluene, 4-ethyl toluene, trimethyl benzene (e.g., 1,3,5-trimethyl benzene, 1,2,4-trimethyl benzene, 1,2,3-trimethyl benzene, etc.), ethylbenzene, styrene, cumene, methylbenzene, propylbenzene, xylenes (e.g., p-xylene, m-xylene, o-xylene, etc.), naphthalene, methyl-naphthalene (e.g., 1-methyl naphthalene, anthracene, 9.10-dimethylanthracene, pyrene, phenanthrene, dimethyl-naphthalene (e.g., 1,5-dimethylnaphthalene, 1,6-dimethylnaphthalene, 2,5-dimethylnaphthalene, etc.), ethyl-naphthalene, hydrindene, methyl-hydrindene, and dymethyl-hydrindene. Single-ring and/or higher ring aromatics may also be produced in some embodiments. Aromatics also include single and multiple ring compounds that contain heteroatom substituents, ie phenol, cresol, benzofuran, etc.

Biomass

As used herein, the term "biomass" is given its conventional meaning in the art and is used to refer to any organic source of energy or chemicals that is renewable. Its major components can be: (1) trees (wood) and all other vegetation; (2) agricultural products and wastes (corn, fruit, garbage ensilage, etc.); (3) algae and other marine plants; (4) metabolic wastes (manure, sewage), and (5) cellulosic urban waste. Examples of biomass materials are described, for example, in Huber, G. W. et al, "Synthesis of Transportation Fuels from Biomass: Chemistry, Catalysts, and Engineering," Chem. Rev. 106, (2006), pp. 4044-4098.

Biomass is conventionally defined as the living and recently dead biological material that can be converted for use as fuel or for industrial production. The criterion as biomass is that the material should be recently participating in the carbon cycle so that the release of carbon in the combustion process results in no net increase averaged over a reasonably short period of time (for this reason, fossil fuels such as peat, lignite and coal are not considered biomass by this definition as they contain carbon that has not participated in the carbon cycle for a long time so that their combustion results in a net increase in atmospheric carbon dioxide). Most commonly, biomass refers to plant matter grown for use as biofuel, but it also includes plant or animal matter used for production of fibers, chemicals or heat. Biomass may also include biodegradable wastes or byproducts that can be burnt as fuel or converted to chemicals, including municipal wastes, green waste (the biodegradable waste comprised of garden or park waste, such as grass or flower cuttings and hedge trimmings), byproducts of farming including animal manures, food processing wastes, sewage sludge, black liquor from wood pulp or algae. Biomass excludes organic material which has been transformed by geological processes into substances such as coal, oil shale or petroleum. Biomass is widely and typically grown from plants, including miscanthus, spurge, sunflower, switchgrass, hemp, corn (maize), poplar, willow, sugarcane, and oil palm (palm oil) with the roots, stems, leaves, seed husks and fruits all being potentially useful. The particular plant or other biomass source used is not important to the product chemical or fuel although the processing of the raw material for introduction to the processing unit will vary according to the needs of the unit and the form of the biomass.

Biomass-Derived

Any of the products, processes, and/or systems described herein may be additionally characterized by the fact that they are biomass-derived, meaning that the products are at least partly derived from biomass, and, in most cases are 100% derived from biomass. As is well-known, the presence of biomass-derived material can be readily ascertained by the presence of 14 C, which is essentially not present in fossil fuels.

Biomass Feed Particle Sizes

The hydrocarbonaceous material in the feed composition may comprise a solid, liquid, and/or gas. In cases where the hydrocarbonaceous material includes solids, the solids may be of any suitable size. In some cases, it may be advantageous to use hydrocarbonaceous solids with relatively small particle sizes. Small-particle solids may, in some instances, react more quickly than larger solids due to their relatively higher surface area-to-volume ratios compared to larger solids. In addition, small particle sizes may allow for more efficient heat transfer within each particle and/or within the reactor volume. This may prevent or reduce the formation of undesired reaction products. Moreover, small particle sizes may provide for increased solid-gas and solid-solid contact, leading to improved heat and mass transfer.

Biomass Pyrolysis Liquid

Biomass pyrolysis liquid or bio-oil is the liquid fraction that can be isolated from a pyrolysis reaction of biomass. Biomass pyrolysis liquid is usually dark brown and approximates to biomass in elemental composition. It is composed of a very complex mixture of oxygenated hydrocarbons with an appreciable proportion of water from both the original moisture and reaction product. Compositionally, the biomass pyrolysis oil will vary with the type of biomass, but is known to consist of oxygenated low molecular weight alcohols (e.g., furfuryl alcohol), aldehydes (aromatic aldehydes), ketones (furanone), phenols (methoxy phenols) and water. Solid char may also be present, suspended in the oil. The liquid is formed by rapidly quenching the intermediate products of flash pyrolysis of hemicellulose, cellulose and lignin in the biomass. Chemically, the oil contains several hundred different chemicals in widely varying proportions, ranging from formaldehyde and acetic acid to complex, high molecular weight phenols, anhydrosugars and other oligosaccharides. It has a distinctive odor from low molecular weight aldehydes and acids, is usually acidic with a pH of 1.5-3.8, and can be an irritant.

Catalysts

Catalyst components useful in the context of this invention can be selected from any catalyst known in the art, or as would be understood by those skilled in the art. Catalysts promote and/or effect reactions. Thus, as used herein, catalysts lower the activation energy (increase the rate) of a chemical process, and/or improve the distribution of products or intermediates in a chemical reaction (for example, a shape selective catalyst). Examples of reactions that can be catalyzed include: dehydration, dehydrogenation, isomerization, hydrogen transfer, aromatization, decarbonylation, decarboxylation, aldol condensation, and combinations thereof. Catalyst components can be considered acidic, neutral or basic, as would be understood by those skilled in the art.

For fast catalytic pyrolysis, particularly advantageous catalysts include those containing internal porosity selected according to pore size (e.g., mesoporous and pore sizes typically associated with zeolites), e.g., average pore sizes of less than about 100 Angstroms, less than about 50 Angstroms, less than about 20 Angstroms, less than about 10 Angstroms, less than about 5 Angstroms, or smaller. In some embodiments, catalysts with average pore sizes of from about 5 Angstroms to about 100 Angstroms may be used. In some embodiments, catalysts with average pore sizes of between about 5.5 Angstroms and about 6.5 Angstroms, or between about 5.9 Angstroms and about 6.3 Angstroms may be used. In some cases, catalysts with average pore sizes of between about 7 Angstroms and about 8 Angstroms, or between about 7.2 Angstroms and about 7.8 Angstroms may be used.

In some preferred embodiments of CFP, the catalyst may be selected from naturally occurring zeolites, synthetic zeolites and combinations thereof. In certain embodiments, the catalyst may be a ZSM-5 zeolite catalyst, as would be understood by those skilled in the art. Optionally, such a catalyst can comprise acidic sites. Other types of zeolite catalysts include: ferrierite, zeolite Y, zeolite beta, modernite, MCM-22, ZSM-23, ZSM-57, SUZ-4, EU-1, ZSM-11, (S)A1P0-31, SSZ-23, among others. In other embodiments, non-zeolite catalysts may be used; for example, $WO_x/ZrO_2$, aluminum phosphates, etc. In some embodiments, the catalyst may comprise a metal and/or a metal oxide. Suitable metals and/or oxides include, for example, nickel, palladium, platinum, titanium, vanadium, chromium, manganese, iron, cobalt, zinc, copper, gallium, and/or any of their oxides, among others. In some cases promoter elements chosen from among the rare earth elements, i.e., elements 57-71, cerium, zirconium or their oxides for combinations of these may be included to modify activity or structure of the catalyst. In addition, in some cases, properties of the catalysts (e.g., pore structure, type and/or number of acid sites, etc.) may be chosen to selectively produce a desired product.

Catalysts for other processes, such as alkylation of olefins are well-known and can be selected for the treatment processes described herein.

Catalyst Residence Time

The catalyst residence time of the catalyst in the reactor is defined as the volume of the reactor filled with catalyst divided by the volumetric flow rate of the catalyst through the reactor. For example, if a 3-liter reactor contains 2 liters of catalyst and a flow of 0.4 liters per minute of catalyst is fed through the reactor, i.e., both fed and removed, the catalyst residence time is 2/0.4 minutes, or 5 minutes.

Contact Time

Contact time is the residence time of a material in a reactor or other device, when measured or calculated under standard conditions of temperature and pressure, i.e., 0° C. and 1 atm. For example, a 2-liter reactor to which is fed 3 standard liters per minute of gas has a contact time of ⅔ minute, or 40 seconds for that gas. For a chemical reaction, contact time or residence time is based on the volume of the reactor, where substantial reaction is occurring, and would exclude volume where substantially no reaction is occurring, such as an inlet or an exhaust conduit. For catalyzed reactions, the volume of a reaction chamber is the volume where catalyst is present.

Conversion

The term "conversion of a reactant" refers to the reactant mole or mass change between a material flowing into a reactor and a material flowing out of the reactor divided by the moles or mass of reactant in the material flowing into the reactor. For example, if 100 grams of ethylene are fed to a reactor and 30 grams of ethylene are flowing out of the reactor, the conversion is [(100−30)/100]=70% conversion of ethylene.

Fluid

The term "fluid" refers to a gas, a liquid, a mixture of a gas and a liquid, or a gas or a liquid containing dispersed solids, liquid droplets and/or gaseous bubbles. The terms "gas" and "vapor" have the same meaning and are sometimes used interchangeably. In some embodiments, it may be advantageous to control the residence time of the fluidization fluid in the reactor. The fluidization residence time of the fluidization fluid is defined as the volume of the reactor divided by the volumetric flow rate of the fluidization fluid under process conditions of temperature and pressure.

Fluidized Bed Reactor

As used herein, the term "fluidized bed reactor" is given its conventional meaning in the art and is used to refer to reactors comprising a vessel that can contain a granular solid material (e.g., silica particles, catalyst particles, etc.), in which a fluid (e.g., a gas or a liquid) is passed through the granular solid material at velocities sufficiently high as to suspend the solid material and cause it to behave as though it were a fluid. The term "circulating fluidized bed reactor" is also given its conventional meaning in the art and is used to refer to fluidized bed reactors in which the granular solid material is passed out of the reactor, circulated through a line in fluid communication with the reactor, and recycled back into the reactor.

Bubbling fluidized bed reactors and turbulent fluidized bed reactors are also known to those skilled in the art. In bubbling fluidized bed reactors, the fluid stream used to fluidize the granular solid material is operated at a sufficiently low flow rate such that bubbles and voids are observed within the volume of the fluidized bed during operation. In turbulent fluidized bed reactors, the flow rate of the fluidizing stream is higher than that employed in a bubbling fluidized bed reactor, and hence, bubbles and voids are not observed within the volume of the fluidized bed during operation.

Examples of fluidized bed reactors, circulating fluidized bed reactors, bubbling and turbulent fluidized bed reactors are described in Kirk-Othmer Encyclopedia of Chemical Technology (online), Vol. 11, Hoboken, N.J.: Wiley¬ Interscience, c2001-, pages 791-825, and in "Fluidization Engineering", $2^{nd}$ Edition, by D. Kunii and O. Levenspiel, Butterworth-Heinemann, 1991, Newton, Mass., both of which are incorporated herein by reference.

Olefins

As used herein, the terms "olefin" or "olefin compound" (a.k.a. "alkenes") are given their ordinary meaning in the art, and are used to refer to any unsaturated hydrocarbon containing one or more pairs of carbon atoms linked by a double bond. Olefins include both cyclic and acyclic (aliphatic) olefins, in which the double bond is located between carbon atoms forming part of a cyclic (closed-ring) or of an open-chain grouping, respectively. In addition, olefins may include any suitable number of double bonds (e.g., monoolefins, diolefins, triolefins, etc.). Examples of olefin compounds include, but are not limited to, ethene, propene, allene (propadiene), 1-butene, 2-butene, isobutene (2 methyl propene), butadiene, and isoprene, among others. Examples of cyclic olefins include cyclopentene, cyclohexane, cycloheptene, among others. Aromatic compounds such as toluene are not considered olefins; however, olefins that include aromatic moieties are considered olefins, for example, benzyl acrylate or styrene.

Pore Size

Pore size relates to the size of a molecule or atom that can penetrate into the pores of a material. As used herein, the term "pore size" for zeolites and similar catalyst compositions refers to the Norman radii adjusted pore size well known to those skilled in the art. Determination of Norman radii adjusted pore size is described, for example, in Cook, M.; Conner, W. C., "How big are the pores of zeolites?" Proceedings of the International Zeolite Conference, 12th, Baltimore, Jul. 5-10, 1998; (1999), 1, pp 409-414, which is incorporated herein by reference in its entirety. As a specific exemplary calculation, the atomic radii for ZSM-5 pores are about 5.5-5.6 Angstroms, as measured by x-ray diffraction. In order to adjust for the repulsive effects between the oxygen atoms in the catalyst, Cook and Conner have shown that the Norman adjusted radii are 0.7 Angstroms larger than the atomic radii (about 6.2-6.3 Angstroms).

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005, incorporated herein by reference in its entirety. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195, which is incorporated herein by reference in its entirety. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, 1998, both incorporated herein by reference in their entirety.

In some embodiments, a screening method is used to select catalysts with appropriate pore sizes for the conversion of specific pyrolysis product molecules. The screening method may comprise determining the size of pyrolysis product molecules desired to be catalytically reacted (e.g., the molecule kinetic diameters of the pyrolysis product molecules). One of ordinary skill in the art can calculate, for example, the kinetic diameter of a given molecule. The type of catalyst may then be chosen such that the pores of the catalyst (e.g., Norman adjusted minimum radii) are sufficiently large to allow the pyrolysis product molecules to diffuse into and/or react with the catalyst. In some embodiments, the catalysts are chosen such that their pore sizes are sufficiently small to prevent entry and/or reaction of pyrolysis products whose reaction would be undesirable.

Pyrolysis

As used herein, the terms "pyrolysis" and "pyrolyzing" are given their conventional meaning in the art and are used to refer to the transformation of a compound, e.g., a solid hydrocarbonaceous material, into one or more other substances, e.g., volatile organic compounds, gases and coke, by heat, preferably without the addition of, or in the absence of, $O_2$. Preferably, the volume fraction of $O_2$ present in a pyrolysis reaction chamber is 0.5% or less. Pyrolysis may take place with or without the use of a catalyst. "Catalytic pyrolysis" refers to pyrolysis performed in the presence of a catalyst, and may involve steps as described in more detail below. Example of catalytic pyrolysis processes are outlined, for example, in Huber, G. W. et al, "Synthesis of Transportation Fuels from Biomass: Chemistry, Catalysts, and Engineering," Chem. Rev. 106, (2006), pp. 4044-4098.

Residence Time.

Residence time is defined as the volume of the reactor or device, or specific portion of a device, divided by the exit flow of all gases out of the reactor, or device or portion of the reactor or device, including fluidization gas, products, and impurities, measured or calculated at the average temperature of the reactor or device and the exit pressure of the reactor or device or portion thereof.

Selectivity

The term "selectivity" refers to the amount of production of a particular product in comparison to a selection of products. Selectivity to a product may be calculated by dividing the amount of the particular product by the amount of a number of products produced. For example, if 75 grams of aromatics are produced in a reaction and 20 grams of benzene are found in these aromatics, the selectivity to benzene amongst aromatic products is 20/75=26.7%. Selectivity can be calculated on a mass basis, as in the aforementioned example, or it can be calculated on a carbon basis, where the selectivity is calculated by dividing the amount of carbon that is found in a particular product by the amount of carbon that is found in a selection of products. Unless specified otherwise, for reactions involving biomass as a reactant, selectivity is on a mass basis. For reactions involving conversion of a specific molecular reactant (ethene, for example), selectivity is the percentage (on a mass basis unless specified otherwise) of a selected product divided by all the products produced.

Yield

The term yield is used herein to refer to the amount of a product flowing out of a reactor divided by the amount of reactant flowing into the reactor, usually expressed as a percentage or fraction. Yields are often calculated on a mass basis, carbon basis, or on the basis of a particular feed component. Mass yield is the mass of a particular product divided by the weight of feed used to prepare that product. For example, if 500 grams of biomass is fed to a reactor and 45 grams of benzene is produced, the mass yield of benzene would be 45/500=9% benzene. Carbon yield is the mass of carbon found in a particular product divided by the mass of carbon in the feed to the reactor. For example, if 500 grams of biomass that contains 40% carbon is reacted to produce 45 grams of benzene that contains 92.3% carbon, the carbon yield is [(45*0.923)/(500*0.40)]=20.8%. Carbon yield from biomass is the mass of carbon found in a particular product divided by the mass of carbon fed to the reactor in a particular feed component. For example, if 500 grams of biomass containing 40% carbon and 100 grams of $CO_2$ are reacted to produce 40 g of benzene (containing 92.3% carbon), the carbon yield on biomass is [(40*0.923)/(500*0.40)]=18.5%; note that the mass of $CO_2$ does not enter into the calculation.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components.

In some embodiments, the feed composition (e.g., in feed stream 6 of FIG. 1) comprises a mixture of hydrocarbonaceous material and a catalyst. The mixture may comprise, for example, solids, liquids, and/or gases. In certain embodiments, the mixture comprises a composition of a solid catalyst and a solid hydrocarbonaceous material. In other embodiments, a catalyst may be provided separately from the reactor feed stream. In some embodiments the feed may be kept in an inert atmosphere or an atmosphere formed by the vent gases from the process, 74.

In some embodiments, for example when solid hydrocarbonaceous materials are used, moisture may optionally be removed from the feed composition prior to being fed to the reactor, e.g., by an optional dryer 10. Removal of moisture from the feed stream may be advantageous for several reasons. For example, the moisture in the feed stream may require additional energy input in order to heat the feed to a temperature sufficiently high to achieve pyrolysis. Variations in the moisture content of the feed may lead to difficulties in controlling the temperature of the reactor. In addition, removal of moisture from the feed can reduce or eliminate the need to process the water during later processing steps.

In some embodiments, the feed composition may be dried until the feed composition comprises less than 10%, less than 5%, less than 2%, or less than 1% water by weight. Suitable equipment capable of removing water from the feed composition is known to those skilled in the art. As an example, in one set of embodiments, the dryer comprises an oven heated to a particular temperature (e.g., at least 80° C., at least 100° C., at least 150° C., or higher) through which the feed composition is continuously, semi-continuously, or periodically passed. In some cases, the dryer may comprise a vacuum chamber into which the feed composition is processed as a batch. Other embodiments of the dryer may combine elevated temperatures with vacuum operation. The dryer may be integrally connected to the reactor or may be provided as a separate unit from the reactor.

In some instances, the particle size of the feed composition may be reduced in an optional grinding system 12 prior to passing the feed to the reactor. In some embodiments, the average diameter of the ground feed composition exiting the grinding system may comprise no more than about 50%, not more than about 25%, no more than about 10%, no more than about 5%, no more than about 2% of the average diameter of the feed composition fed to the grinding system. Large-particle feed material may be more easily transportable and less difficult to process than small-particle feed material. On the other hand, in some cases it may be advantageous to feed small particles to the reactor (as discussed below). The use of a grinding system allows for the transport of large-particle feed between the source and the process, while enabling the feed of small particles to the reactor.

Suitable equipment capable of grinding the feed composition is known to those skilled in the art. For example, the grinding system may comprise an industrial mill (e.g., hammer mill, ball mill, etc.), a unit with blades (e.g., chipper, shredder, etc.), or any other suitable type of grinding system. In some embodiments, the grinding system may comprise a cooling system (e.g., an active cooling systems such as a pumped fluid heat exchanger, a passive cooling system such as one including fins, etc.), which may be used to maintain the feed composition at relatively low temperatures (e.g., ambient temperature) prior to introducing the feed composition to the reactor. The grinding system may be integrally connected to the reactor or may be provided as a separate unit from the reactor. While the grinding step is shown following the drying step in FIG. 1, the order of these operations may be reversed in some embodiments. In still other embodiments, the drying and grinding steps may be achieved using an integrated unit.

In some cases, grinding and cooling of the hydrocarbonaceous material may be achieved using separate units. Cooling of the hydrocarbonaceous material may be desirable, for example, to reduce or prevent unwanted decomposition of the feed material prior to passing it to the reactor. In one set of embodiments, the hydrocarbonaceous material may be passed to a grinding system to produce a ground hydrocarbonaceous material. The ground hydrocarbonaceous material may then be passed from the grinding system to a cooling system and cooled. The hydrocarbonaceous material may be cooled to a temperature of lower than about 300° C., lower than about 200° C., lower than about 100° C., lower than about 75° C., lower than about 50° C., lower than about 35° C., or lower than about 20° C. prior to introducing the hydrocarbonaceous material into the reactor. In embodiments that include the use of a cooling system, the cooling system includes an active cooling unit (e.g., a heat exchanger) capable of lowering the temperature of the biomass. In some embodiments, two or more of the drier, grinding system, and cooling system unit operations may be combined into a single unit. The cooling system may be, in some embodiments, directly integrated with one or more reactors.

As illustrated in FIG. 1, the feed composition may be transferred to reactor 20. The feed may be kept under an inert atmosphere such as the vent gas 74 or other suitable gas. Fluids such as recycle gas 2, vent gas 74 or other fluids may be fed along with the solid hydrocarbonaceous feed into reactor 20 in order to facilitate smooth feed flow. Optionally a portion of the aqueous phase 84 or organic phase 94 may be fed along with the hydrocarbonaceous feed. Aqueous phase 84 or organic phase 94 may optionally be combined to be fed to reactor 20 or may be fed separately.

The reactor may be used, in some instances, to perform catalytic pyrolysis of hydrocarbonaceous material. In the illustrative embodiment of FIG. 1, the reactor comprises any suitable reactor known to those skilled in the art. For example, in some instances, the reactor may comprise a continuously stirred tank reactor (CSTR), a batch reactor, a semi-batch reactor, or a fixed bed catalytic reactor, among others. In some cases, the reactor comprises a fluidized bed reactor, e.g., a circulating fluidized bed reactor, a moving bed reactor such as a riser reactor, or a bubbling bed reactor or turbulent bed reactor. Fluidized bed reactors may, in some cases, provide improved mixing of the catalyst and/or hydrocarbonaceous material during pyrolysis and/or subsequent reactions, which may lead to enhanced control over the reaction products formed. The use of fluidized bed reactors may also lead to improved heat transfer within the reactor. In addition, improved mixing in a fluidized bed reactor may lead to a reduction of the amount of coke adhered to the catalyst, resulting in reduced deactivation of the catalyst in some cases. Throughout this specification, various compositions are referred to as process streams; however, it should be understood that the processes could also be conducted in batch mode.

In the set of embodiments illustrated in FIG. 1, separated catalyst may exit the solids separator via stream 42. In some cases, the catalyst exiting the separator may be at least partially deactivated. The separated catalyst 42 may be fed, in some embodiments, to a regenerator 30 in which any catalyst that was at least partially deactivated may be re-activated. Used catalyst also exits reactor 20 via stream 22 so that a flow of catalyst through the reactor is established. The separated catalyst 42 may be combined with used catalyst stream 22 before feeding to regenerator 30. In some embodiments, the regenerator may comprise optional purge stream 38, which may be used to purge coke, ash, and/or catalyst from the regenerator. Methods for activating and regenerating catalyst are well-known to those skilled in the art, for example, as described in *Kirk-Othmer Encyclopedia of Chemical Technology* (Online), Vol. 5, Hoboken, N.J.: Wiley-Interscience, 2001, pages 255-322.

In one set of embodiments, an oxidizing agent is fed to the regenerator via a stream 32, e.g., as shown in FIG. 1. The oxidizing agent may originate from any source including, for example, a tank of oxygen, atmospheric air, or steam, among others. In the regenerator, the catalyst is re-activated by reacting the catalyst with the oxidizing agent. In some cases, the deactivated catalyst may comprise residual carbon and/or coke, which may be removed via reaction with the oxidizing agent in the regenerator. The regenerator in FIG. 1 comprises a vent stream 34 which may include regeneration reaction products, residual oxidizing agent, etc. The vent stream from the regenerator may be passed through a catalytic exhaust gas cleanup system to further reduce the concentrations of CO and hydrocarbons to reduce emissions vented to the atmosphere. Portions of the vent stream 34 may be recycled to the gas feed 32 of the regenerator 30 to control the heat release of the regeneration process.

The regenerator may be of any suitable size mentioned above in connection with the reactor or the solids separator. In addition, the regenerator may be operated at elevated temperatures in some cases (e.g., at least about 300° C., 400° C., 500° C., 600° C., 700° C., 800° C., or higher). The residence time of the catalyst in the regenerator may also be controlled using methods known by those skilled in the art, including those outlined above. In some instances, the mass flow rate of the catalyst through the regenerator will be coupled to the flow rate(s) in the reactor and/or solids separator in order to preserve the mass balance. or heat balance. or both heat and mass balance in the system.

As shown in the illustrative embodiment of FIG. 1, the regenerated catalyst may exit the regenerator via stream 36. The regenerated catalyst may be recycled back to the reactor. In some cases, catalyst may be lost from the system during operation or catalyst may be removed as it deactivates. In some such and other cases, additional "makeup" catalyst may be added to the system from fresh catalyst inventory 4. As shown illustratively in FIG. 1, the regenerated and makeup catalyst may be fed to the reactor via a separate stream, or the regenerated and makeup catalyst may be fed with the fluidization fluid via recycle stream 8, or any selected combination of these.

Referring back to solids separator 40 in FIG. 1, the reaction products (e.g., fluid hydrocarbon products) exit the solids separator via stream 44. In some cases, a fraction of stream 44 may be purged. The contents of the purge stream may be fed to a combustor or a water-gas shift reactor, for example, to recuperate energy that would otherwise be lost from the system. Preferably, the reaction products in stream 44 may be fed to condenser 50. The condenser may comprise a heat exchanger which condenses at least a portion of the reaction products from a gaseous to a liquid state. The condenser may be used to separate the reaction products into gaseous, liquid, and solid fractions. The condenser may be a series of condensers operated at different temperatures and flow rates rather than a single unit. The operation of condensers is well known to those skilled in the art. Examples of condensers are described in more detail in *Perry's Chemical Engineers' Handbook*, Section 11: "Heat Transfer Equipment." 8th ed. New York: McGraw-Hill, 2008.

The condenser may also, in some embodiments, make use of pressure change to condense portions of the product stream. In FIG. 1, stream 52 may comprise the liquid fraction of the reaction products (e.g., water, aromatic compounds, olefin compounds, etc.), and stream 54 may comprise the gaseous fraction of the reaction products (e.g., CO, CO2, H2, methane, ethylene, propylene, butenes, etc.). In some embodiments, the gaseous fraction may be fed to a vapor recovery system 70. The vapor recovery system may be used, for example, to recover any selected vapors within stream 54 and transport them via stream 72. Stream 72 may be combined with product stream 92 for further purification or as feed to further upgrading. In addition, stream 74 may be used to transport CO, CO2, H2, methane, and/or other non-recoverable gases from the vapor recovery system. It should be noted that, in some embodiments, the optional vapor recovery system may be placed in other locations.

Other products (e.g., excess gas) may be transported to optional compressor 100 via stream 76, where they may be compressed and used as fluidization gas in the reactor (stream 102) and/or where they may assist in transporting the hydrocarbonaceous material to the reactor.

In some embodiments, the liquid fraction is further processed to separate the water phase from the organic phase in separator 60 in FIG. 1. Aqueous phase 62 obtained from liquids separator 60 may be sent to waste water cleanup or the organic components present in 62 may be further concentrated in separator 80, for example by membrane separation or distillation or osmotic separation or other methods known to those skilled in the art, to obtain a more concentrated stream 84 and a less concentrated stream 82. Stream 84 that is more concentrated in hydrocarbonaceous materials may be recycled back to reactor 20 for further upgrading to useful and valuable products via catalytic fast pyrolysis.

Organic phase 64 may optionally be fed to a product separator 90. Product separation in 90 can separate the organic materials into a crude product 92 that is enriched in the desired components for transport to further purification or processing, and a crude material 94 that is relatively depleted of useful materials. Stream 94 can be recycled back to reactor 20 for further upgrading via catalytic fast pyrolysis to produce additional useful products or it can be used as fuel or otherwise disposed of.

As shown in FIG. 1 streams 84 and 94 may be combined or may be separately fed to reactor 20. Streams 84 and 94 may be combined to be added to the biomass feed or either 84 or 94 may be separately mixed with the biomass for introduction into reactor 20.

It should be understood that, while the set of embodiments described by FIG. 1 includes a reactor, solids separator, regenerator, condenser, etc., not all embodiments will involve the use of these elements. For example, in some embodiments, the feed stream may be fed to a catalytic fixed bed reactor, reacted, and the reaction products may be collected directly from the reactor and cooled without the use of a dedicated condenser. In some instances the product may be fed to a quench tower to which is fed a cooling fluid, preferably a liquid, along with the product stream to cool and condense the products. In some instances, while a dryer, grinding system, solids separator, regenerator, condenser, and/or compressor may be used as part of the process, one or more of these elements may comprise separate units not fluidically and/or integrally connected to the reactor. In other embodiments, one or more of the dryer, grinding system, solids separator, regenerator, condenser, and/or compressor may be absent. In some embodiments, the desired reaction product(s) (e.g., liquid aromatic hydrocarbons, olefin hydrocarbons, gaseous products, etc.) may be recovered at any point in the production process (e.g., after passage through the reactor, after separation, after condensation, etc.).

In general, the invention can be any apparatus, process, or integrated system having one or any combination of the features discussed in this specification.

Figure 2:
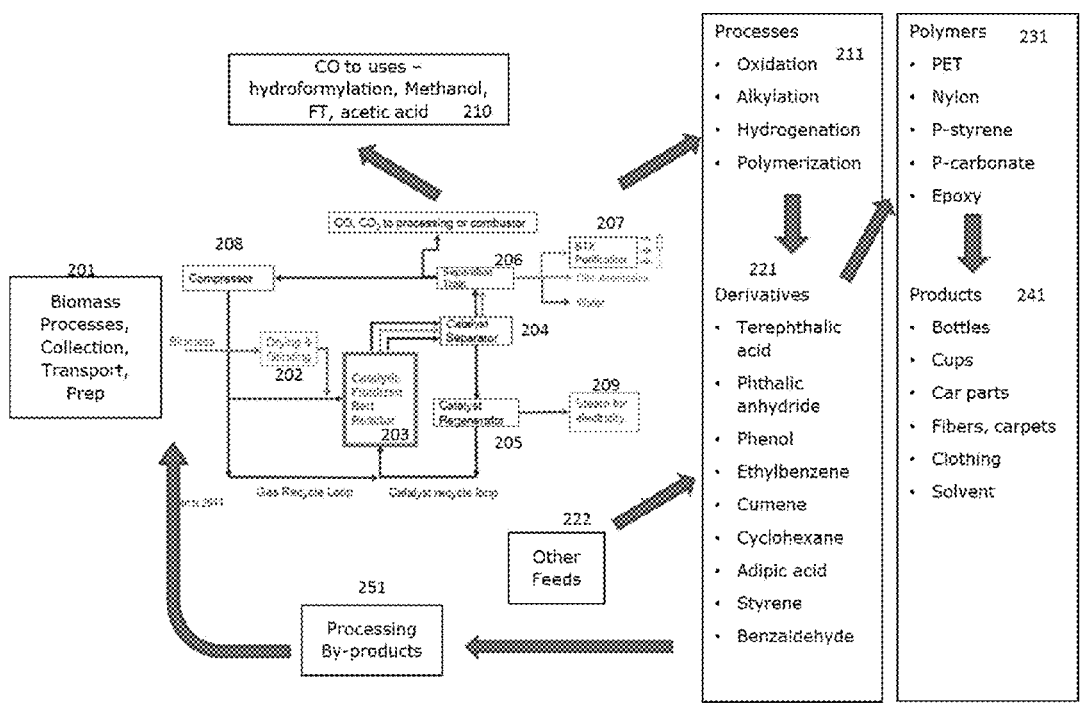
FIG. 2 illustrates processes for converting biomass to chemical intermediates incorporating catalytic fast pyrolysis.

FIG. 2 presents a flow diagram of the production of a variety of chemical intermediates labeled as derivatives, polymers, and products from biomass by the process of the instant invention. In FIG. 2 the biomass feed and processes that conduct biomass to the biomass upgrading plant are designated as 201, processes for preparing the biomass for conversion in the CFP process are shown as 202, and the catalytic fast pyrolysis is indicated as 203. Collection and separation of the fluid hydrocarbons comprises a catalyst separator, 204, catalyst regenerator, 205, product separator 206, purification of aromatics 207, gas recycle compressor, 208, and electrical generator 209. Items 201 through 207, and optionally 208 and 209, comprise the elements of the CFP process that produces fluid hydrocarbon products. The fluid hydrocarbon products (primary products) are upgraded in a variety of ways, including 1) gas upgrading processes as shown in 210 that include hydroformylation, methanol synthesis, Fischer-Tropsch synthesis, and acetic acid production, and 2) aromatics or aromatics and olefin upgrading processes as shown in 211 that optionally utilize additional reactants as other feeds 222 and produce chemical intermediates (secondary products) as shown as 221, 231, and 241. Processes that produce the chemical intermediates are secondary processes, typically conducted in primary product upgrading reactors isolated from the CFP reactor although in some cases the CFP and primary product upgrading reactors could be integrated. By-products of the secondary upgrading processes can be collected as processing by-products 251 and recycled to the CFP process either in combination with the stream arising from 201 or 202, or with the catalyst recycle from 205, or from the gas recycle from compressor 208 that feed into the CFP reactor, 203, or some combination of these.

DESCRIPTION OF SOME PREFERRED EMBODIMENTS

Condensation of condensable materials from the pyrolysis products occurs by passing them through a condensation train to condense and collect the desired products as liquid phases. Typically, the condensation train will comprise one or more chilled water condensers, one or more electrostatic precipitator and one or more coalescence filter, as are well known in the art, all of which will be connected in series. While the order of the condensers can be varied, it is typical that the first condenser is a water cooled condenser with temperatures on the water side of 15 to 35 C. Additional condensers can be used that are chilled to lower temperatures, for example, from −10 C to 15 C. Condensation can also be effected by quenching the product mixture with a liquid quench stream, typically water or an organic phase such as a heavy organic, for example, the less valuable reaction products. All gases that pass through the condensation train may also be collected at the end of the train.

In most embodiments, two liquid phases are condensed from a pyrolysis reactor, an aqueous phase and an organic phase. The aqueous phase comprises a significant fraction of the condensed phases, for example, the condensed aqueous phase may comprise 20 to 80 mass % of the condensed phases, in some embodiments, 35 to 65 mass % of the condensed phases. The organic phase may (and typically does) comprise small amounts of dissolved water as well. The percent water in a liquid phase can be measured by known methods such as NMR (nuclear magnetic resonance), HPLC (high performance liquid chromatography), gas chromatography, or by fractional distillation. Preferably, the mass % water in an organic phase is determined by Karl Fisher titration.

In some embodiments, the aqueous liquid phase is treated such that one or more organic components are removed, and the resulting liquid, now enriched in water, is recycled to a pyrolysis reactor. More preferably, water is removed from the aqueous phase and a water-depleted stream is recycled to the pyrolysis reactor. In some preferred embodiments, the aqueous phase is treated to have at least 10 mass % less water, in some embodiments at least 30% less water, in some embodiments, at least 50% less water, and in some embodiments, 30 to 80% less water. Water can be removed from the aqueous phase by any suitable method including distillation, absorption, filtration, osmosis, membrane separation, or any other process.

In some embodiments the liquid organic phase is separated into a crude fraction enriched in useful products and a second fraction relatively depleted in useful products. Separations of organic liquids can be accomplished by distillation, adsorption, membrane separation, osmosis or any other process. The fraction that is relatively depleted in useful products can be optionally recycled to the pyrolysis reactor.

The distillation of either the water or organic phases can be accomplished by conventional methods using conventional distillation equipment such as tray, bubble cap, packed columns or the like. Distillation may be carried out at subatmospheric pressures or at atmospheric pressures. Ordinarily, this distillation will be carried out at subatmospheric pressures with pressures of 1 to 75 kPa being preferred. It is, of course, understood that where separations of the carbonaceous product or the recycle stream are made to narrow the recycle stream by excluding water, the above preferred pressures may be somewhat less preferred. The method of distillation, as well as pressures and other conditions are not to be held limiting to the present invention since the choice of such methods to provide the desired splits in the catalytically pyrolyzed products are well within the ability of those skilled in the art. In some cases the heavier products will be recycled, in other cases the lighter products will be recycled. With these teachings, one skilled in the art will find little difficulty in providing the equipment and conditions for obtaining these recycle fractions by distillation.

Adsorption of the organics dissolved in or suspended in an aqueous phase can be accomplished by passing the aqueous phase through a bed of organic materials such as solid biomass, coked catalyst, char, or the like. The organics in the aqueous phase are preferentially adsorbed on the bed of organic materials and the water-enriched aqueous phase passes through. The organics-enriched biomass or other organics adsorbent can be fed back to the pyrolysis reactor.

Adsorption of the water dissolved in or suspended in an organic phase can be accomplished by contacting the organic phase with a bed of water adsorbent materials or passing the organic phase through a bed of water adsorbent materials such as silica gel, magnesium sulfate, clays, zeolites or the like at modest temperatures, ie less than 200 C, or less than 100 C, or less than 50 C, to remove the water. The organic-enriched phase passes through the adsorbent or remains above the adsorbent. The organic phase can be fed back to the pyrolysis reactor.

A filtration process can be used to separate suspended solids from an aqueous or organic phase before, after, or independent of any adsorption process to remove suspended solids or adsorbent materials. Filtration techniques are well known to those skilled in the art. Membrane separation of the organic and aqueous materials in the aqueous or organic phases can be accomplished by contacting the liquid phase with a permselective membrane in a batch or continuous process. Continuous processing according to the invention is achievable wherein an aqueous solution feed stream containing organic components is passed on one side and in contact with a hydrophobic, polymeric membrane having selectivity for the organic components, while a solution sink or vapor vacuum is in contact with the permeate side of the membrane. The lower chemical potential of, for example, the organic component solution sink together with counter current relationship of the organic aqueous solution feed stream, provides driving force for permeating organics through these selective membranes into the organic solution sink. The organic enriched solution sink or vapor can be swept or moved by physical means to suitable processing which promotes the recycling of the organics and any complexing solutions. Suitable complexing solutions could be derived from organic fractions of the reaction product including aromatics, phenols, olefins or the like. The membrane permeation step is preferably operated under ambient conditions of temperature which can vary over a wide range from about −50° C. to about 250° C. depending upon the selection of the sweep liquid and the thermal condition of the feed mixture. Higher operating temperatures are frequently desirable because of the increased rates of permeation, however, lower temperatures may be desired to reduce energy input.

The permeation membrane is non-porous, that is, free from holes and tears and the like, which destroy the continuity of the membrane surface. Useful membranes are typically organic, polymeric materials. The membranes are preferably in as thin a form as possible which permits sufficient strength and stability for use in the permeation process. Generally separation membranes from about 0.1 to about 15 mils or somewhat more are utilized. High rates of permeation are obtained with thinner membranes which can be supported with structures such as fine mesh wire, screen, porous metals, and ceramic materials. The membrane may be a simple disc or sheet of the membrane substance which is suitably mounted in a duct or pipe, or mounted in a plate and framed filter press. Other forms of membrane may also be employed such as hollow tubes and fibers through which or around which the feed is applied or is recirculated with the permeate being removed at the other side of the tube as a sweep liquid phase. Various other useful shapes and sizes readily adaptable to commercial installations are known to those skilled in the art. A particularly advantageous method of separating and concentrating water soluble organics is to filter the aqueous solution through a layer of biomass so that the organics are absorbed by the biomass. The organics-impregnated biomass can be further dried or otherwise treated and fed to the reactor for CFP upgrading. In this way the organics from the water soluble fraction are converted to valuable products, including aromatics (BTXN), olefins, CO, CO2, phenol and other valuable materials. After filtering through the biomass, the aqueous solution can be discarded or passed to a water treatment process.

Catalyst components for the CFP process can be selected from any catalyst known in the art, or as would be understood by those skilled in the art. Functionally, catalysts may be limited only by the capability of any such material to promote and/or effect dehydration, dehydrogenation, isomerization, hydrogen transfer, aromatization, decarbonylation, decarboxylation, aldol condensation and/or any other reaction or process associated with or related to the pyrolysis of a hydrocarbonaceous material. Catalyst components can be considered acidic, neutral or basic, as would be understood by those skilled in the art.

The invention is generally applicable to any biomass pyrolysis reaction. Preferably, the biomass feedstock comprises a solid hydrocarbonaceous material. The biomass feedstock may comprise, for example, any one or combination of the biomass sources that are mentioned in the Glossary section. The pyrolysis reactor can be without a solid catalyst; however, preferably, the pyrolysis reactor comprises a solid catalyst for catalytic fast pyrolysis (CFP). The type of reactor and the type of solid catalyst (if present) are not limited, and can be generally of the type known for conversion of biomass to fluid hydrocarbonaceous streams. Examples of suitable apparatus and process conditions for CFP are described in U.S. Pat. No. 8,277,643 of Huber at al. and in the US Patent Application 20130060070A1 of Huber et al. that are fully incorporated herein by reference. Conditions for CFP of biomass can be selected from any one or any combination of the following features (which are not intended to limit the broader aspects of the invention): a zeolite catalyst, a ZSM-5 catalyst; a zeolite catalyst comprising one or more of the following metals: titanium, vanadium, chromium, manganese, iron, cobalt, nickel, copper, zinc, gallium, platinum, palladium, silver, phosphorus, sodium, potassium, magnesium, calcium, tungsten, zirconium, cerium, lanthanum, and combinations thereof; a fluidized bed, circulating bed, or riser reactor; an operating temperature in the range of 300° to 1000° C.; and/or a solid catalyst-to-biomass mass ratio of between 0.1 and 20.

Alkylation

In some embodiments a benzene-rich fraction is separated from the catalytic fast pyrolysis process and upgraded in a primary product upgrading process comprising the catalytic alkylation of benzene with ethylene to produce ethylbenzene or the catalytic alkylation of benzene with propylene to produce cumene, or some combination of these. In practicing some embodiments of this invention, a portion of the effluent of the alkylation reaction zone is reintroduced into the alkylation reaction zone to enhance the yield of useful products via transalkylation, A polyethylbenzene, such as diethylbenzene, triethylbenzene, and so forth up to even hexaethylbenzene, is a preferred transalkylating agent because each can transalkylate to ethylbenzene, regardless of whether each is alkylated by ethylene. It would be preferred to not recycle to the alkylation reaction zone a stream containing more than 75 wt-% ethylbenzene, such as the product stream produced by an ethylbenzene column of the product separation zone.

In embodiments that include the alkylation of benzene by olefins, the ratio of the weight of the olefin entering the alkylation catalyst bed in the olefinic feed stream per unit time to the sum of the weights of compounds entering the alkylation catalyst bed per the same unit time, multiplied by 100, is generally less than 1.88, preferably less than 1.3, and more preferably less than 0.01. This ratio is sometimes referred to herein as the olefin ratio. The alkylation conditions may comprise a maximum olefin concentration based on the weight of compounds entering the alkylation catalyst bed of preferably less than 1.88 wt-%, most preferably less than 1.3 wt-%, and still more preferably less than 0.01 wt-%.

The aromatic feed stream and the olefinic feed stream are preferably combined upstream of the alkylation catalyst bed. The alkylation reaction zone can comprise one or more alkylation catalyst beds and/or one or more alkylation catalyst reactors, and each reactor may contain one or more alkylation catalyst beds. A common configuration of an alkylation zone employs two alkylation reactors, each of which has two alkylation catalyst beds. The number of alkylation reactors is typically less than eight, and the number of catalyst beds in a given alkylation reactor is typically less than six.

Alkylation conditions for this invention include a molar ratio of phenyl groups per alkyl group of typically from 25:1 to about 1:1. In some embodiments, the molar ratio may be less than 1:1, and may be down to 0.75:1 or lower. Preferably, the molar ratio of phenyl groups per ethyl group (or per propyl group, in cumene production) is below 6:1, and in some embodiments, in the range of 4:1 to 2:1.

In general, for a given molar ratio of alkylation substrate per alkylation agent, especially an olefinic alkylation agent, the greater the molar ratio of phenyl groups to alkyl groups in the feed stream, the less is the rise in temperature in the reaction zone that occurs as a result of the alkylation reactions. Although the reactor may have indirect heat exchange means to remove the heat as it is produced, the reactor is preferably adiabatic, and so the outlet temperature of the effluent stream is higher than the inlet temperature of the reactants. The appropriate reaction temperature may be preferably from 100° C. to the critical temperature of the alkylation substrate, which may be 475° C. or even higher, the inlet temperature in the reaction zone is generally from 200 to 260° C., and preferably from 230 to 250° C. The temperature rise is typically from 5 to 50° C., and preferably less than 20° C. The temperature rise in the reaction zone may be controlled by adjusting the molar ratio of phenyl groups to ethyl groups in the feed stream, for example by recycling portions of the reactor effluent. Recycling reactor effluent to the reaction zone of the alkylation reactor does not interfere in a significant way with the extent of the alkylation or transalkylation reactions, and recycling reactor effluent may be employed for the purpose of controlling reaction zone temperatures.

Alkylation is preferably performed in the liquid phase. Consequently, reaction pressure needs to be sufficiently high to ensure at least a partial liquid phase. Where ethylene is the olefin, the pressure range for the reactions is usually from about 200 to about 1000 psi(g) (1379 to 6985 kPa(g)), more commonly from about 300 to about 600 psi(g) (2069 to 4137 kPa(g)), and even more commonly from about 450 to about 600 psi(g) (3103 to 4137 kPa(g)). Preferably, the reaction conditions are sufficient to maintain benzene in a liquid phase and are supercritical conditions for ethylene. For olefins other than ethylene, this invention may be practiced generally at a pressure of from 50 to 1000 psi(g) (345 to 6985 kPa(g)).

The weight hourly space velocity (WHSV) of ethylene preferably ranges from 0.01 to 2.0 hr-1. The WHSV of aromatics, including benzene and a polyalkylaromatic having at least two C2+ groups, if any, preferably ranges from 0.3 to 480 hr$^{-1}$. In a preferred embodiment, in which the polyalkyl aromatic is a diethylbenzene or a triethylbenzene, the molar ratio of benzene per ethylene is from 2:1 to 6:1, the WHSV of ethylene is from 0.1 to 1.0 hr$^{-1}$, and the WHSV of aromatics, including benzene and the polyethylbenzenes is from 0.5 to 19 hr$^{-1}$.

In practicing some embodiments of this invention, the alkylation reactor effluent stream is separated into at least two portions, in order that one portion can be recycled and passed to the alkylation reaction zone. In some embodiments a portion of the alkylation effluent is recycled to the catalytic fast pyrolysis reactor along with, or separate from, any primary products of the fast catalytic pyrolysis process.

In some embodiments, when one portion of the alkylation effluent is recycled to and introduced into an alkylation reaction zone or the CFP reactor, at least one other portion of the alkylation effluent passes to a separation zone for recovering the monoalkyl aromatic. The separation zone may comprise a benzene fractionation column in order to recycle unreacted benzene to the alkylation zone, and an ethylbenzene fractionation column in order to recover ethylbenzene as product from the heavier polyalkylbenzenes. A polyalkylbenzene fractionation column may also be used in order to separate diethylbenzenes and triethylbenzenes from the other higher mass polyalkylbenzenes, particularly where the polyalkylbenzene that is present in the feed stream is a diethylbenzene or a triethylbenzene. The separation zone preferably does not comprise a deethanizer unless the concentrations of unreacted ethylene, ethane, or light C3-paraffins in the reactor effluent are high enough to justify a step of separating these components from the alkylation reactor effluent stream.

In addition to producing a fraction comprising the monoalkyl aromatic, the separation zone may also produce one or more other fractions of the alkylation effluent from a portion of the alkylation effluent. Accordingly, as an alternative to, or in addition to recycling a portion of the alkylation effluent to the alkylation reaction zone, some or all of at least one of these other fractions recovered from the separation zone can also passed to the alkylation reaction zone or to the CFP process. These other recovered fractions can comprise polyethylbenzenes, which in turn can be recycled to the alkylation reaction zone as transalkylation agents. In some embodiments, several process streams produced by the separation zone can be used to supply such polyethylbenzenes to the alkylation reaction zone.

The catalyst for the alkylation process may be any alkylation catalyst that is not deactivated rapidly as a consequence of recycling the polyalkyl aromatic to the alkylation reactor. The catalyst for the alkylation process may comprise one or more aluminosilicate molecular sieves known as zeolites. Zeolitic molecular sieves are suitable for use in the present invention are crystalline aluminosilicates which in the calcined form typically may be represented by the general formula:

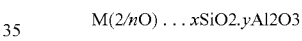

$$M(2/nO)\ldots xSiO2.yAl2O3$$

where Me is a cation, n is the valence of the cation, x has a value of from about 5 to 200, and y has a value of from about 2 to 10. The above formula is merely a typical representation; however, less common zeolite formulations, such as those having lower proportions of aluminum or the presence of additional elements, may also be used. Detailed descriptions of zeolites may be found in D. W. Breck, Zeolite Molecular Sieves, John Wiley and Sons, New York 1974, and in other standard references.

The preferred alkylation catalyst for use in the alkylation process is a zeolitic catalyst. Suitable zeolites include zeolite beta, Zeolite Y, ZSM-5, PSH-3, MCM-22, MCM-36, MCM-49, and MCM-56. Zeolite beta is described in U.S. Pat. No. 3,308,069 and Re 28,341. The topology of zeolite beta and the three zeolite beta polytypes are described in the article by Higgins, et al., in Zeolites, Vol. 8, November 1988, starting at page 446; and in the letter by M. M. J. Treacy et al., in Nature, Vol. 332, Mar. 17, 1988, starting at page 249. Suitable zeolite betas include, but are not limited to, the naturally occurring mixture of the three polytypes, any one of the three polytypes, or any combination of the three polytypes. The use of zeolite beta in alkylation and transalkylation is disclosed in U.S. Pat. Nos. 4,891,458 and 5,081,323, and the use of pristine zeolite beta in alkylation is disclosed in European Pat. EP 432,814 B1. Suitable zeolite betas include, but are not limited to, pristine zeolite beta in which the H+ ion has at least partially replaced the contained metal cation, as disclosed in European Pat. EP 432,814 B1; and zeolite beta into which certain quantities of alkaline, alkaline-earth, or metallic cations have been introduced by ion exchange, as disclosed in U.S. Pat. No. 5,672,799. Various modifications of zeolite beta are also suitable for use in this invention. Suitable modified zeolite betas include, but are not limited to, zeolite beta which has been modified by steam treatment and ammonium ion treatment, as disclosed in U.S. Pat. No. 5,522,984; and zeolite beta in which the H+ ion has at least partially replaced the contained metal cation, with the zeolite beta being modified by isomorphous substitution of aluminum by boron, gallium, or iron, as disclosed in European Pat. EP 432,814 B1.

It is believed that mordenite zeolite and omega zeolite can also be suitable catalysts for the alkylation process. Suitable zeolites are zeolite beta as disclosed in U.S. Pat. Nos. 4,891,458 and 5,081,323, and a steamed and ammonium exchanged zeolite beta as disclosed in U.S. Pat. No. 5,522,984. A preferred zeolite beta for use in alkylation process in this invention is disclosed in U.S. Pat. No. 5,723,710. Any of the US patents mentioned herein are incorporated herein by reference.

The olefin for the reaction can come partly or entirely from the pyrolysis reaction. In this way, it is possible to synthesize styrene in an integrated process using exclusively or primarily (at least 50% by mass, more preferably at least 90% and still more preferably at least 95% by mass) biomass-derived materials.

In some embodiments, the alkylation is conducted in the same process stream as the CFP reaction but at a later stage where alkylation catalyst is present; and in some embodiments, the alkylation is conducted in the same process stream with olefin added in stages along the length of the CFP reaction process stream. In some embodiments, alkylation is conducted in a separate reactor, and occurs after the steps of a CFP reaction and solids removal (such as in a cyclone) and the catalyst for the CFP reaction and the alkylation reaction can be combined and regenerated together.

An additional advantage to combining the CFP process with an alkylation process is that relatively small amounts of olefin can be used (for example, less than 2%, less than 1% or less than 0.5% by mass of the CFP product stream), thus reducing undesired side products, such as 1,1-diphenylethane, and the remaining CFP products collected. The overall result is upgrading the value of products from the CFP process without significantly increasing the amount of undesired by-products. In some cases, desired alkylated product, such as ethylbenzene is produced while fewer undesired by-products are produced. Yet another advantage may be that reacting a product stream from the CFP reaction, such as the product stream in an upper portion (for example, above the bottom half) of the fluidized bed reactor, or before any separation, or after partial separation (such as after removing solids, or after removing solids and separating an aqueous phase) while result in little or no increase in undesired product since any so-called side products (such as 1,1-DPE) can be captured with an aromatic fraction for use as a fuel or recycled to the CFP reactor. Thus, several potential advantages are created by combining alkylation with the CFP process in an integrated system.

An integrated process may also involve staged addition of an olefin along the upward direction of a fluidized bed reactor where one or more trays of catalyst comprise a mixture of catalyst, with some catalyst selected to increase conversion of biomass or biomass-derived components (such as cellulose or cellulose fragments) into smaller molecules and some catalyst selected to increase the alkylation of aromatics with olefin; thus, in some preferred embodiments, a fluidized bed reactor comprises a plurality of trays distributed along the length of the reactor (typically oriented perpendicular to gravity) with catalyst composition varying between one or more trays; in some embodiments with a relatively higher percentage of alkylation catalyst nearer the top of the reactor. Although it is recognized that there is often a similarity between CFP catalyst and alkylation catalyst, the skilled worker can easily identify catalysts that are relatively superior for alkylations (for example, this could be done from reading the literature or conducting simple comparative testing).

Styrene

Alkylbenzenes produced by the alkylation of benzene derived from the CFP process can be further upgraded to styrene. Examples of these alkyl benzenes are ethylbenzene, cumene (isopropyl benzene), n-propyl benzene, secondary butyl benzene, isobutyl benzene, tertiary butyl benzene, n-butyl benzene, the amyl benzenes, the hexyl benzenes, the heptyl benzenes, the octyl benzenes, and the nonyl benzenes. Higher alkyl benzenes are also obtainable from the alkylation of benzene with the corresponding olefin. The higher alkylated products also can either be straight chain or branched chain. In general, the alkylated benzenes having more than 4 carbon atoms in their side chains are less desirable as feed stocks since a large proportion of such compounds are converted to cracked gases which require separation and recovery. Cumene is particularly desirable as is secondary butyl benzene. The latter compound produces two useful products, namely, styrene and ethylene. The cracking is preferably carried out at temperatures in the range of from 600° to 850° C. and preferably from 700° to 800° C. Pressure preferably ranges from 0.25 to 10 atmospheres (Absolute pressure, i.e., ata) with 0.5 to 5 atmospheres being preferred and 0.5 to 1 being most preferred.

The dehydrogenation of ethylbenzene to styrene in a fluid-bed or fixed-bed reactor/regenerator system, in the presence of a catalyst based on an iron oxide and further promoters, selected, e.g., from metal oxides such as alkaline oxides, earth-alkaline metal oxides and/or oxides of the metals of the group of lanthanides, supported on a modified alumina is envisioned as part of an integrated reactor system.

The dehydrogenation reaction of ethylbenzene to styrene is carried out at temperatures generally ranging from 540 to 630° C. A typical styrene production unit comprises several adiabatic reactors in series, with intermediate heating steps at a temperature ranging from 540° C. to 630° C. and with contact times in the order of tenths of a second; a radial flow reactor which operate under vacuum at a pressure ranging from 30.39 to 50.65 Kpa (absolute Pascal) (0.3 to 0.5 ata); and water vapor which is fed with the charge to be dehydrogenated.

Dehydrogenation of ethylbenzene to styrene can also be conducted in an oxidative process in the presence of oxygen containing feed to aid in the removal of the hydrogen as water or other material and shift the equilibrium towards the production of styrene. The oxygen containing feed can be oxygen gas, nitrogen oxides, hydrogen peroxide, $CO_2$, air, sulfur oxide(s), or various oxygenated hydrocarbon compounds (acids, esters, alcohols, ketones).

Thus, the invention can include the synthesis of styrene and, optionally, the use of styrene for the production of polystyrenes (GPPS crystals, high impact HIPS and expandable EPS), acrylonitrile-styrene-butadiene (ABS) and styrene-acrylonitrile (SAN) copolymers and styrene-butadiene rubbers (SBR) is envisioned as part of the integrated reactor system.

In some embodiments, the styrene reactor is in thermal contact with the catalyst regeneration reactor for the CFP process so that some heat from the catalyst regeneration is transferred to the process of dehydrogenating an alkylbenzene. In some embodiments, a hot product stream from the CFP reaction is passed over a dehydrogenation catalyst (preferably iron oxide) and a portion of the alkylbenzenes in the CFP stream are converted to styrene; preferably, ethylbenzene is added to the stream prior to or during passage over the dehydrogenation catalyst—this can create a variety of advantages such as cooling the product stream (thus reducing the need for heat exchanging condensers), extending catalyst life with no or a reduced need to heat added steam, and increasing the efficiency and decreasing the size of apparatus.

Phenol

Phenol is a basic commodity chemical with many end uses that can be prepared from the cumene derived from products of CFP benzene alkylation with propylene. Cumene is oxidized in air or with another oxidizing agent to give cumene hydroperoxide, which is subsequently cleaved by acid to provide phenol and acetone. The phenol and acetone are separated and each one purified to the degree necessary to satisfy its ultimate use. An integrated process from biomass includes the recycle of byproducts of phenol production such as acetone to the CFP process wherein they can be converted to additional aromatics, or olefins, or both.

Phenol is among the primary products of the CFP process for converting biomass to useful chemical intermediates. Separation of phenol from the product mixture can be accomplished by a range of techniques including distillation, solvent extraction, extractive distillation, crystallization, membrane separation, or other processes well known to those skilled in the art, or some combination of these.

Phenol can be further upgraded into a self-hardening phenolic resin by reacting phenol and formaldehyde. Phenol derivatives can be made by reaction with a wide range of aldehydes. A hybrid phenolic/polysiloxane resin can be prepared by reacting phenol with an alkoxy or silanol functional siloxane polymer or an aldehyde and further reacting the reaction product thereof with an aldehyde, or with an alkoxy or silanol functional siloxane polymer, the sequence depending on the desired composite resin. Phenol resin byproducts can be recycled to the CPF process to improve overall process efficiency, except wherein a silanol or other Si-containing material has been introduced, therein producing an integrated reactor process that includes CFP and several subsequent processes.

Additional secondary products that can be derived from phenol include alkylphenols, polymethylphenols, ethylphenols, isopropylphenols, sec-butylphenols, tert-butylphenols, tert-pentylphenols, cycloalkylphenols, aralkylphenols, alkenylphenols, indanols, catechol, trihydroxybenzenes, pyrogallol, hydroxyhydroquinone, phloroglucinol, bisphenols (bishydroxyarylalkanes, such as bis-phenol A (BPA)), hydroxybiphenyls, and phenol ethers. Other useful secondary products derived from phenol include diphenylcarbonate, Diphenyl carbonate can be produced by reacting phenol with carbon monoxide that is also derived from the CFP process, thus producing a fully bio-derived diphenylcarbonate. Production of polycarbonates from bio-derived materials can be conducted by the transesterification from BPA and diphenyl carbonate: The processes that are used to produce secondary and tertiary products from phenol can produce waste streams that can in part be recycled to the feed of the CFP process for conversion to additional useful materials. Polycarbonates that are not suitable for further production of consumer products can be ground to appropriate size particles and recycled to the CFP process, thus increasing carbon efficiency of the overall process.

Cyclohexane

A benzene-enriched stream obtained from the CFP process can be converted to cyclohexane by the catalytic hydrogenation of benzene, either through liquid phase hydrogenation, catalyzed, for example, with Ni Raney at 150° C. and about 15 atmosphere pressures (Sabatier, Ind. Eng. Chem. 18, 1005 (1925)) or through the process developed by the Institut Francais du Petrole wherein benzene and hydrogen-rich gas is fed to a liquid-phase reactor containing Raney nickel catalyst. The nickel suspension is circulated to improve heat removal, the benzene being completely hydrogenated in a second fixed-bed reactor. Said catalytic hydrogenation of benzene can also be carried out by hydrogenation in gas phase, catalyzed with noble metals, mainly platinum supported over alumina, etc., at 200° C. temperatures and about 30 kg/cm2 pressures. Benzene production technologies enable the obtention of high purity benzene, being its purity degree of over 99.99%. Hence, cyclohexane that is thus obtained by hydrogenation could have similar purity levels. However, hydrogenation reactions take place along with secondary reactions that produce undesired contaminants especially methylcyclopentane (MCP). In an integrated process that converts biomass to chemicals, byproducts such as MCP can be recycled to the CFP reactor for upgrading to additional aromatics and olefins.

Adipic Acid

Adipic acid is a large volume commodity chemical used for the production of polymeric compounds. Cyclohexane derived from benzene produced in a CFP process can be used as a precursor for the manufacture of adipic acid. A variety of techniques can be used to convert cyclohexane to adipic acid.

As is well-known, in the oxidation of cyclohexane to adipic acid in the presence of a cobalt salt, any cobalt salt of an organic acid can be used, see U.S. Pat. No. 3,231,608 to Kollar. Adipic acid is prepared from cyclohexane using cobalt as a catalyst, often in the presence of initiators (U.S. Pat. No. 4,032,569; U.S. Pat. No. 4,263,453 and Japanese Pat. No. 51075018. U.S. Pat. No. 4,032,569, U.S. Pat. No. 5,221,800). Preferably at least about 25 millimols of cobalt be present per mole of cyclohexane in the process and that temperature be in the range of from about 85° C. to about 105° C., oxygen partial pressure at least about 150 psia, preferably for a period of about 0.5 to about 3 hours. Chromium, manganese, and/or copper may also be used in place or, or in addition to the cobalt catalyst. In some cases. cyclohexane is first converted to cyclohexanone and cyclohexanol, and nitric acid can be used to convert these to adipic acid.

Alternatively, cyclohexane can be converted to adipic acid over a solid heterogeneous catalyst, such as Au, Pd, Pt, Ru and/or Ag on an oxide support. See, for example, U.S. Pat. Pub. 2012/0095258.

An alternative process is the reaction of cyclohexane with hydrogen peroxide in a continuous reactor. See, for example, Wen et al, "A continuous process for the production of adipic acid via catalytic oxidation of cyclohexane with H2O2," Green Chem. 2012, 2868-2875.

Any of these processes can be integrated with the production of cyclohexane from pyrolysis of biomass. For example, it is known that the addition of water to the synthesis can improve the oxidation of cyclohexane to adipic acid (see U.S. Pat. No. 5,221,800); and in an integrated process, water resulting from the biomass pyrolysis is added to the reaction mixture, for example water produced in a biomass drying step or water produced from the pyrolysis. The water may be used with or without purification. Thus, what is conventionally considered waste water may be used to improve a synthesis process and reduce waste. In another example, "waste" phenol resulting from the biomass pyrolysis can be hydrogenated and the resulting cyclohexanone and/or cyclohexanol combined with the cyclohexane to adipic acid process (either in the initial feed or at an intermediate stage); thus reducing waste and increasing yield of adipic acid.

Nylon 6,6

Subsequently, nylon-6,6 can be made by the reaction of adipic acid with hexamethylenediamine (HMD). It is also known that polyamides, such as nylon-6,6, can be produced by reaction of diamines and dinitriles in the presence of water. In an integrated process from biomass to chemicals undesired byproducts from the synthesis or subsequent reaction of nylon-6,6, such as monomers and lower polymers, can be recycled to the CFP reactor to produce additional aromatics, thus increasing the efficiency of the overall integrated process.

In some cases, at least a portion of the HMD is made with nitrogen derived from the biomass that is fed to the primary reactor. In some preferred embodiments, the nylon is made in a downward direction and there is heat exchange with either the CFP reactor or the system for reactivating catalyst.

Toluene Disproportionation

A toluene-rich fraction separated from the primary product mixture may be disproportionated to provide a higher value mixture of xylenes and benzene. The xylene product produced has the equilibrium composition of approximately 24 percent of 1,4-(para-xylene), 54 percent of 1,3-(meta-xylene), and 22 percent of 1,2-isomer (ortho-xylene). Of the xylene isomers, meta-xylene is normally the least desired product, with ortho and para-xylene being the more useful products. Para-xylene is of particular value, being useful in the manufacture of terephthalic acid which is an intermediate in the manufacture of synthetic fibers such as polyesters, ie polyethylene terephthalate ester (PET). Selectivity to p-xylene can be enhanced by selection of an appropriate catalyst such as modified ZSM-5, see U.S. Pat. No. 6,133,470, and can generally be obtained by treatment of a molecular sieve type catalyst such as a zeolite, ALPO or SAPO with an organosilicon modifying agent. The disproportionation of a toluene-rich fraction may be carried out at temperatures ranging from about 200° C. to about 600° C. or above and at pressures ranging from atmospheric to perhaps 100 atmospheres or above. The toluene-rich feedstock may be supplied to the reaction zone containing the zeolite catalyst at rates providing relatively high space velocities. The toluene weight hourly space velocity (WHSV) may be greater than 1. Hydrogen is supplied to the reaction zone at a hydrogen/toluene mole ratio within the range of 3-6. The hydrogen pressure may be 500 psi or more. The toluene feedstock need not be rigorously dried before supplying it to the reaction zone and water contents may exceed 100 ppm.

Enhanced p-Xylene Formation in the CFP Process

The proportion of p-xylene in the CFP process can be increased by using a p-xylene selective catalyst in an CFP reactor. This may be done either in a primary reactor that directly pyrolyzes biomass or in a secondary reactor that treats at least a portion of the products from the primary reactor. This catalyst may have dual functionality, catalyzing both the conversion of biomass and enhancing the proportion of p-xylene.

Terephthalic Acid

A para-xylene rich fraction separated from the primary product mixture or a subsequent product mixture, or some combination of these can be integrated with a process for producing terephthalic acid (TPA) wherein the para-xylene rich fraction is oxidized to produce terephthalic acid. The TPA thus produced may also be esterified, e.g., to dimethyl terephthalate in the same or separate reactor.

The intermediate product stream containing p-xylene is oxidized to terephthalic acid in a secondary process with a second catalyst. There is no need for purification of the intermediate product stream to remove ortho-xylene or ethylbenzene. The second catalyst is any catalyst which catalyzes oxidation of p-xylene to terephthalic acid, e.g., heavy metal catalyst such as cobalt and/or manganese, and which optionally may include a catalyst for esterification to dimethyl terephthalate. Advantageously, a costly xylene separation step to be eliminated and the product stream of the first contacting can be directly integrated with the oxidation process to pure terephthalic acid or dimethyl terephthalate.

The production of terephthalic acid can be integrated with a CFP process that produces a para-xylene rich stream or with the para-xylene separated from a toluene disproportion process in an integrated system, or both. One process for producing terephthallic acid is the so-called Amoco process described, e.g., in U.S. Pat. No. 2,833,816. This process involves liquid phase air oxidation of p-xylene using multivalent (heavy) metals, particularly cobalt and manganese as catalyst in an acetic acid solvent and with bromine as a renewable source of free radicals. The terephthalic acid product crystals are recovered, e.g., by centrifugation, and purified by dissolving the crystals in water contacting with a hydrogenation catalyst, e.g., noble metal on a carbon support, and again recovering the crystals. Dimethyl terephthalate can be produced by liquid phase esterification of the terephthalic acid using metal catalysts such as zinc, molybdenum, antimony and tin with a large excess of methanol.

In another process for producing terephthalic acid, four steps are used, alternating oxidation and esterification to produce dimethyl terephthalate, as described, e.g., in British Patent Specification Nos. 727,989 and 809,730. First, p-xylene is oxidized with a molecular oxygen-containing gas (air) in a liquid phase in the presence of a heavy metal catalyst such as cobalt, manganese, or mixture of both to produce p-toluic acid (PTA) which is esterified with methanol to produce methyl p-toluate (MPT). A second oxidation of the MPT with the same catalyst and molecular oxygen yields in a liquid phase yields monomethyl terephthalate which is esterified to the diester dimethyl terephthalate.

Both terephthalic acid and dimethyl terephthalate are used in the production of polyethylene terephthalate (PET) or other polyesters through a reaction with glycol, e.g., ethylene glycol or tetramethylene glycol. Reaction of biomass derived terephthalic acid or dimethyl terephthalate with biomass derived glycol can be utilized to produce a PET that is virtually 100% biomass derived.

PET produced from biomass by the inventive process can be further formed into synthetic fibers; beverage, food and other liquid containers, thermoform plastic materials; and engineering resins in combination with glass or other fiber.

Byproducts of the terephthalic acid production processes, or of the polymerization processes to produce PET can be recycled to the CFP reactor to produce additional aromatics, olefins, or both olefins and aromatics, thus greatly increasing the carbon efficiency of the integrated process.

Multistage Reactor

Any of the processes described herein for making intermediates can be conducted in a multistage reactor. Thus, the invention includes any selected process conducted in a multistage reactor. For example, the process can be conducted with the CFP process conducted in the first stage(s) of a multistage, fluidized bed reactor with catalyzed disproportion of toluene to p-xylene occurring in a later stage. Such a configuration can reduce cost, energy, and/or size of the process. The integration within a single process stream without product separation may also increase yield of desired products, for example by utilizing unstable compounds or other intermediates that would not be available after a separation step.

EXAMPLES

The following examples demonstrate that by-products of the production of chemical intermediates can be recycled to a CFP process along with biomass to produce additional aromatics and olefins. In these examples furfural, which has $H/C_{eff}=0$, is used as a model compound for the reactions of biomass.

Example 1

Furfural

A down-flow fixed bed reactor was fitted with 3.0 g of a commercial spray-dried ZSM-5 catalyst containing 50 wt % ZSM-5 and a silica binder. The reactor was heated to 575 C under a flow of N2. A solution of liquid furfural was fed to the reactor at a rate of 1.23 g/hr (WHSV=0.41 hr-1) by means of an HPLC pump. The liquid entered the 0.5 inch diameter tubular reactor from the top through a 1/16 inch diameter tube and was carried along with a flow of $N_2$ of 97 ml/min. The catalyst bed was held in place in the reactor tube with a plug of quartz wool below the catalyst. The product of the reaction was passed into a gas bag.

The flow of furfural was started and continued for 25 minutes, with the produce gases collected for 5, 5-minute time intervals during feed flow, and one 5-minute time interval after the feed flow was stopped and only $N_2$ was flowing. The contents of the 6 gas bags was analyzed by GC with a Shimadzu (GC-2014 model) equipped with TCD and FID detectors, and 40 meter Rts-vms capillary column from Restek. The analyses of the 6 samples were combined and calculations of the product yields, selectivities, and mass and carbon balances were conducted. Coke deposited on the catalyst was quantified by using a thermogravimetric analyzer (TGA) from Shimadzu (TGA-50 model). The data are presented in Table 1.

Example 2

Acetone

The experiment in example 1 was repeated with a fresh charge of catalyst and a flow of acetone of 0.81 g/hr (WHSV=0.27 hr-1). The results are included in Table 1.

Example 3

Furfural and Acetone Mixture

The experiment in Example 1 was repeated with a fresh charge of catalyst and a mixture of furfural and acetone containing 62 weight % furfural and 38 wt % acetone used as the feed. The flow of the feed mixture was 1.2 g/hr (WHSV=0.40 hr-1). The results are included in Table 1.

Example 4

Hexanol and Hexanoic Acid

The experiment in Example 1 was repeated with a fresh charge of catalyst and a mixture of 47 weight % hexanol and 53 weight % hexanoic acid used as the feed. The flow of the feed mixture was 1.23 g/hr (WHSV=0.41 hr-1). The results are included in Table 1.

Example 5

Furfural, Hexanol, and Hexanoic Acid

The experiment in Example 1 was repeated with a fresh charge of catalyst and a mixture of 47 weight % furfural, 25 weight % hexanol, and 28 weight % hexanoic acid as the feed. The flow of the feed mixture was 1.29 g/hr (WHSV=0.43 hr-1). The results are included in Table 1.

TABLE 1

Experimental results in fixed bed reactor tests

| | Feedstock | | | | |
|---|---|---|---|---|---|
| | Furfural | Acetone | Furfural + Acetone | Hexanol + Hexanoic Acid | Hexanol + Hexanoic Acid + Furfural |
| | | | Example | | |
| | 1 | 2 | 3 | 4 | 5 |
| Temperature (° C.) | 575 | 575 | 575 | 575 | 575 |
| $H/C_{eff}$ | 0.00 | 1.33 | 0.51 | 1.67 | 0.90 |
| Conc. (mol C/mol $N_2$) | 0.259 | 0.176 | 0.261 | 0.287 | 0.288 |
| WHSV ($h^{-1}$) | 0.41 | 0.27 | 0.40 | 0.41 | 0.43 |
| Carbon conversion (%) | 100.0 | 100.0 | 100.0 | 100.0 | 100.0 |
| | Yield (% Carbon) | | | | |
| Aromatics | 27.2 | 40.8 | 31.8 | 33.3 | 29.1 |
| Olefins | 9.3 | 44.7 | 20.1 | 37.4 | 17.7 |
| Methane | 0.8 | 5.1 | 2.0 | 6.3 | 2.9 |
| CO | 34.3 | 3.5 | 18.4 | 5.5 | 12.8 |
| CO2 | 3.8 | 7.9 | 5.1 | 0.4 | 2.0 |
| Coke | 30.7 | 11.0 | 23.4 | 2.8 | 8.2 |
| | Aromatics selectivity (% Carbon) | | | | |
| Benzene | 43.6 | 37.7 | 41.4 | 35.8 | 38.8 |
| Toluene | 44.3 | 46.6 | 45.3 | 46.6 | 45.1 |
| Xylenes | 8.5 | 13.7 | 11.3 | 15.8 | 13.8 |

TABLE 1-continued

Experimental results in fixed bed reactor tests

| | Feedstock | | | | |
|---|---|---|---|---|---|
| | Furfural | Acetone | Furfural + Acetone | Hexanol + Hexanoic Acid | Hexanol + Hexanoic Acid + Furfural |
| | | | Example | | |
| | 1 | 2 | 3 | 4 | 5 |
| Alkyl Benzenes | 0.8 | 1.1 | 0.9 | 1.3 | 1.2 |
| Styrenes | 0.1 | 0.1 | 0.1 | 0.1 | 0.1 |
| Indenes | 0.5 | 0.2 | 0.2 | 0.1 | 0.2 |
| Naphthalenes | 2.3 | 0.7 | 0.8 | 0.3 | 0.8 |
| Olefins selectivity (Carbon %) | | | | | |
| Ethylene | 61.2 | 56.5 | 60.7 | 45.4 | 51.5 |
| Propylene | 34.1 | 38.2 | 34.8 | 47.5 | 42.7 |
| Propadiene/propyne | 0.6 | 1.2 | 0.7 | 1.6 | 1.0 |
| $C_4$ olefins | 4.1 | 4.2 | 3.8 | 4.7 | 4.1 |
| $C_5$ olefins | 0.0 | 0.0 | 0.0 | 0.8 | 0.7 |
| Overall selectivity (Carbon %) | | | | | |
| Aromatics | 25.6 | 36.1 | 31.5 | 38.9 | 40.1 |
| Olefins | 8.7 | 39.5 | 20.0 | 43.7 | 24.4 |
| Oxygenates | 0.03 | 0.00 | 0.02 | 0.00 | 0.02 |
| CO | 32.3 | 3.1 | 18.2 | 6.4 | 17.6 |
| $CO_2$ | 3.6 | 7.0 | 5.1 | 0.4 | 2.7 |
| Methane | 0.7 | 4.5 | 2.0 | 7.3 | 3.9 |
| Coke | 29.0 | 9.7 | 23.2 | 3.3 | 11.3 |
| O/C in feed | 0.400 | 0.333 | 0.375 | 0.25 | 0.32 |
| O/C in Olefins + Aromatics | 0.000026 | 0 | 0.000038 | 0 | 0.000030 |
| H/C in Olefins + Aromatics | 1.31 | 1.57 | 1.44 | 1.57 | 1.44 |

In the table $H/C_{eff}$ is calculated as (moles H − 2 × moles O)/(moles C)

The results in Table 1 show that by-products of chemical processes produce additional aromatics and olefins when fed to a CFP process. Furfural is a potential by-product of biomass upgrading by a variety of biological processes such as fermentation or thermochemical processes such as pyrolysis. Example 1 shows that furfural can be converted in a CFP process to useful aromatics and olefins. In Example 2, acetone, a by-product of phenol production, is shown to convert to aromatics and olefins in a CFP process. Example 3 shows that mixtures of acetone that is a byproduct of further chemical processing of biomass-derived benzene or other aromatics or olefins, can be converted in a single reactor with biological molecules such as furfural, that is representative of biomass. Acetone recycle from a phenol process boosts the yield of aromatics above that observed with biomass alone, as represented by furfural. Example 4 shows that longer chain alcohols and acids such as hexanol and hexanoic acid, that are by-products of adipic acid production or other chemical upgrading processes based on CFP aromatics and olefins, can be recycled and converted to aromatics and olefins in a CFP process. Example 5 shows that a mixture of hexanol and hexanoic acid that is a byproduct of further chemical processing of biomass-derived benzene or other aromatics or olefins, can be converted in a single reactor with biological molecules such as furfural, that is representative of biomass, and that useful aromatics and olefins are obtained. Hexanol and hexanoic acid recycle from an adipic acid process boosts the yield of aromatics above that observed with biomass alone, as represented by furfural.

Each of the Examples 1 through 5 shows that a feedstock that has a high O/C atom ratio can be converted to a product with very low O/C ratio and almost no oxygen in its product aromatics and olefins. Each of Examples 1 through 5 additionally shows that a feedstock with a range of $H/C_{eff}$ ratios from 0 to 1.67 can be converted to a mixture of aromatics and olefins with a high $H/C_{eff}$.

Thus, in preferred embodiments, byproducts from the synthesis of one or more chemical intermediates, which have a $H/C_{eff}$ ratio of from 0 to 1.67, in some embodiments from 0 to 1.0, in some embodiments from 0 to 0.8, in some embodiments from 0 to 0.5 (these are molar ratios, and in the case of a product mixture, this is based on the entire mixture) are fed back to a pyrolysis reactor and are converted to a mixture of aromatics and olefins with a $H/C_{eff}$ of at least 1.0, in some embodiments at least 1.2, and in some embodiments in the ratio of 1.0 or 1.2 to 2.2 or 2.0 or 1.5. Preferably, the mixture of aromatics and olefins has an O/C atomic ratio less than 0.01. These characteristics provide advantages in process efficiency and higher overall yield of desirable chemical intermediates.

What is claimed:

1. A method for producing one or more fluid chemical intermediates from a hydrocarbonaceous material, comprising:
   feeding a hydrocarbonaceous material to a reactor, and catalytically pyrolyzing within the reactor at least a portion of the hydrocarbonaceous material and producing one or more pyrolysis products;
   catalytically reacting at least a portion of the pyrolysis products, separating at least a portion of the hydrocarbon products; and
   reacting a portion of said hydrocarbon products to produce a chemical intermediate; and further wherein:
   (a) wherein the step of reacting a portion of said hydrocarbon products to produce a chemical intermediate produces byproducts; and further wherein at least a portion of the byproducts of the chemical intermediate production are returned to the pyrolysis reactor; or
   (b) a benzene-rich fraction is separated from the hydrocarbon products; and is alkylated with an olefin to produce the chemical intermediate, or is oxidized to produce phenol, or is hydrogenated to produce cyclohexane; or (c) at least a portion of one benzene-rich fraction separated from the hydrocarbon products is hydrogenated to produce cyclohexane, and at least a portion of the cyclohexane is oxidized to adipic acid; or (d) at least a portion of one toluene-rich fraction is separated from the hydrocarbon products; and is subjected to a disproportionation reaction to produce a xylenes-enriched product stream, or is subjected to a methylation reaction to produce a xylenes-enriched product stream; or (e) at least a portion of one para-xylene-rich fraction that is derived from the hydrocarbon products is oxidized to produce terephthalic acid that, optionally, is polymerized to poly(ethylene terephthalate) (PET), poly(butylene terephthalate) (PBT), or poly(trimethylene terephthalate) (PTT); or (f) separating at least a portion of one ortho-xylene rich fraction from the hydrocarbon products and oxidizing said at least a portion of one ortho-xylene rich fraction to produce phthalic anhydride; or (g) at least a portion of one ethylbenzene-rich fraction that is derived from the hydrocarbon products is dehydrogenated to produce styrene that, optionally, is polymerized to polystyrene; or (h) p-xylene is produced and further comprising oxidizing the p-xylene using pyrolysis products other than acetic acid.

2. The method of claim 1 wherein the steps of feeding a hydrocarbonaceous material to a reactor and reacting a portion of said hydrocarbon products to produce a chemical intermediate are conducted within an integrated reactor system.

3. A method for producing one or more fluid chemical intermediates from a hydrocarbonaceous material, comprising:

feeding a hydrocarbonaceous material to a reactor, and pyrolyzing within the reactor at least a portion of the hydrocarbonaceous material and producing one or more pyrolysis products;

catalytically reacting at least a portion of the pyrolysis products, separating at least a portion of the hydrocarbon products;

and reacting a portion of said hydrocarbon products to produce a chemical intermediate;

wherein the steps of feeding a hydrocarbonaceous material to a reactor and reacting a portion of said hydrocarbon products to produce a chemical intermediate are conducted within an integrated reactor system; and wherein the integrated reactor system comprises a biomass conveyor, a catalyst-containing pyrolysis reactor, a primary product separator, a primary product upgrader, and a secondary product separator.

4. The method of claim 1 wherein the pyrolysis products comprise primary products that comprise aromatics and/or olefins, and wherein the chemical intermediates comprise one or more components selected from the group consisting of ethylene oxide, ethanol, acetic acid, acetaldehyde, acrylonitrile, acrylic acid, styrene, cumene, ethyl benzene, terephthalic acid, monomethyl terephthalate, dimethyl terephthalate, polyethyleneterephthalate, polybutylene terephthalate, phthalic anhydride, phenol, ethylbenzene, cyclohexane, adipic acid, benzaldehyde, benzoic acid, hexanes, ethylene glycol, polyethylene, hexamethylenediamine, adiponitrile, Nylon 6, Nylon 6,6, toluene diisocyanate, toluene diamine, methylene diphenyl diisocyanate, polyurethanes, polycarbonates, polystyrenes, acrylonitrile-styrene-butadiene and styrene-acrylonitrile copolymers and styrene-butadiene rubbers, alkylphenols, polymethylphenols, ethylphenols, isopropylphenols, sec-butylphenols, tert-butylphenols, tert-pentylphenols, cycloalkylphenols, aralkylphenols, alkenylphenols, indanols, catechol, trihydroxybenzenes, pyrogallol, hydroxyhydroquinone, phloroglucinol, bisphenols (bishydroxyarylalkanes), hydroxybiphenyls, phenol ethers, phenol-formaldehyde resins, phenolic/polysiloxane resins, fibers, beverage, food and other liquid containers, thermoform plastic materials; and engineering resins and mixtures thereof.

5. The method of claim 1 wherein the step of reacting a portion of said hydrocarbon products to produce a chemical intermediate produces byproducts; and further wherein at least a portion of the byproducts of the chemical intermediate production are returned to the pyrolysis reactor.

6. The method of claim 1 wherein the pyrolysis step is catalytic pyrolysis and further wherein a benzene-rich fraction is separated from the hydrocarbon products; and is alkylated with an olefin to produce the chemical intermediate, or is oxidized to produce phenol, or is hydrogenated to produce cyclohexane.

7. The method of claim 1 wherein the pyrolysis step is catalytic pyrolysis and further wherein at least a portion of one benzene-rich fraction separated from the hydrocarbon products is hydrogenated to produce cyclohexane, and at least a portion of the cyclohexane is oxidized to adipic acid.

8. The method of claim 1 wherein the pyrolysis step is catalytic pyrolysis and further wherein at least a portion of one toluene-rich fraction is separated from the hydrocarbon products; and is subjected to a disproportionation reaction to produce a xylenes-enriched product stream, or is subjected to a methylation reaction to produce a xylenes-enriched product stream.

9. The method of claim 1 wherein the pyrolysis step is catalytic pyrolysis and further wherein at least a portion of one para-xylene-rich fraction that is derived from the hydrocarbon products is oxidized to produce terephthalic acid that, optionally is polymerized to poly(ethylene terephthalate) (PET), poly(butylene terephthalate) (PBT), or poly(trimethylene terephthalate) (PTT).

10. The method of claim 1 wherein the pyrolysis step is catalytic pyrolysis and further comprising separating at least a portion of one ortho-xylene rich fraction is from the hydrocarbon products and oxidizing said at least a portion of one ortho-xylene rich fraction to produce phthalic anhydride.

11. The method of claim 1 wherein the pyrolysis step is catalytic pyrolysis and further wherein at least a portion of one ethylbenzene-rich fraction that is derived from the hydrocarbon products is dehydrogenated to produce styrene that, optionally, is polymerized to polystyrene.

12. The method of claim 1 wherein the pyrolysis step is catalytic pyrolysis and further wherein p-xylene is produced and further comprising oxidizing the p-xylene using pyrolysis products other than acetic acid.

13. A method for producing one or more fluid hydrocarbon products from a hydrocarbonaceous material comprising:

feeding a hydrocarbonaceous material to a reactor;

pyrolyzing within the reactor at least a portion of the hydrocarbonaceous material under reaction conditions sufficient to produce one or more pyrolysis products;
catalytically reacting within the reactor at least a portion of the one or more pyrolysis products under reaction conditions sufficient to produce one or more fluid hydrocarbon products comprising olefins and aromatics;
reacting at least a portion of said fluid hydrocarbon products to produce at least one chemical intermediate; and
feeding at least a portion of the byproducts of the chemical intermediate production back to the pyrolysis reactor.

14. The method of claim 13 wherein the pyrolysis step is catalytic pyrolysis.

15. The method of claim 14 wherein the byproducts comprise acetone and wherein the acetone is fed back to the pyrolysis reactor.

16. The method of claim 14 wherein the byproducts comprise hexanol and hexanoic acid, that are fed back to the pyrolysis reactor.

17. The method of claim 14 wherein the byproducts having a $H/C_{eff}$ ratio of from 0 to 1.67 are fed back to the pyrolysis reactor and are converted to a mixture of aromatics and olefins with a $H/C_{eff}$ of at least 1.0.

18. The method of claim 17 wherein the mixture of aromatics and olefins has a 0/C atomic ratio less than 0.01.

* * * * *